US008911711B2

(12) United States Patent
Hyde et al.

(10) Patent No.: US 8,911,711 B2

(45) Date of Patent: Dec. 16, 2014

(54) METHOD, DEVICE, AND SYSTEM TO CONTROL PH IN PULMONARY TISSUE OF A SUBJECT

(75) Inventors: Roderick A. Hyde, Redmond, WA (US); Muriel Y. Ishikawa, Livermore, CA (US); Jordin T. Kare, Seattle, WA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1172 days.

(21) Appl. No.: 12/286,729

(22) Filed: Sep. 30, 2008

(65) Prior Publication Data

US 2010/0080760 A1 Apr. 1, 2010

Related U.S. Application Data

(63) Continuation-in-part of application No. 12/286,752, filed on Sep. 30, 2008, and a continuation-in-part of application No. 12/286,753, filed on Sep. 30, 2008.

(51) Int. Cl.

| | |
|---|---|
| ***A61K 9/12*** | (2006.01) |
| ***A61M 15/02*** | (2006.01) |
| ***A61M 11/00*** | (2006.01) |
| ***A61M 15/00*** | (2006.01) |

(52) U.S. Cl.

CPC ............. *A61M 15/02* (2013.01); *A61M 11/001* (2014.02); *A61M 15/0003* (2014.02); *A61M 2230/208* (2013.01)

USPC ........................................................... 424/45

(58) Field of Classification Search

CPC .... A61K 9/12; A61M 15/02; A61M 15/0003; A61M 15/001

See application file for complete search history.

(56) References Cited

U.S. PATENT DOCUMENTS

| | | | | |
|---|---|---|---|---|
| 4,054,622 | A | 10/1977 | Lester | |
| 4,186,183 | A | 1/1980 | Steck et al. | |
| 4,217,344 | A | 8/1980 | Vanlerberghe et al. | |
| 4,235,871 | A | 11/1980 | Papahadjopoulos et al. | |
| 4,261,975 | A | 4/1981 | Fullerton et al. | |
| 4,485,054 | A | 11/1984 | Mezei et al. | |
| 4,501,728 | A | 2/1985 | Geho et al. | |
| 4,774,085 | A | 9/1988 | Fidler | |
| 4,789,633 | A | 12/1988 | Huang et al. | |
| 4,837,028 | A | 6/1989 | Allen | |
| 4,895,719 | A * | 1/1990 | Radhakrishnan et al. | 424/45 |
| 4,946,787 | A | 8/1990 | Eppstein et al. | |
| 5,049,388 | A * | 9/1991 | Knight et al. | 424/450 |
| 5,192,528 | A | 3/1993 | Radhakrishnan et al. | |
| 5,628,981 | A | 5/1997 | Liversidge et al. | |
| 5,786,214 | A | 7/1998 | Holmberg | |
| 5,965,434 | A | 10/1999 | Wolff et al. | |
| 6,080,791 | A | 6/2000 | Bodian et al. | |
| 6,117,449 | A | 9/2000 | See et al. | |
| 6,132,893 | A | 10/2000 | Schöning et al. | |
| 6,143,420 | A | 11/2000 | Heimann et al. | |
| 6,187,332 | B1 | 2/2001 | Gern et al. | |
| 6,197,835 | B1 | 3/2001 | Gañan-Cálvo | |
| 6,267,310 | B1 | 7/2001 | Cappola | |
| 6,301,247 | B1 | 10/2001 | Larson et al. | |
| 6,426,086 | B1 | 7/2002 | Papahadjopoulos et al. | |
| 6,464,940 | B1 | 10/2002 | Akioka et al. | |
| 6,466,133 | B1 | 10/2002 | Skardon | |
| 6,504,841 | B1 | 1/2003 | Larson et al. | |
| 6,596,305 | B1 | 7/2003 | Edgerly-Plug | |
| 6,716,636 | B1 | 4/2004 | Schneider et al. | |
| 6,897,196 | B1 | 5/2005 | Szoka, Jr. et al. | |
| 7,009,169 | B2 | 3/2006 | Wong et al. | |
| 7,119,900 | B2 | 10/2006 | Okumura et al. | |
| 7,181,345 | B2 | 2/2007 | Rosenfeld et al. | |
| 7,208,314 | B2 | 4/2007 | Monahan et al. | |
| 7,213,465 | B2 | 5/2007 | Benzel et al. | |
| 7,229,973 | B2 | 6/2007 | Bae et al. | |
| RE39,871 | E | 10/2007 | Skardon | |
| 7,285,243 | B2 | 10/2007 | Springston et al. | |
| 7,334,845 | B2 | 2/2008 | Peterson et al. | |
| 7,348,453 | B2 | 3/2008 | Rozema et al. | |
| 7,383,071 | B1 | 6/2008 | Russell et al. | |
| 7,682,920 | B2 | 3/2010 | Herner | |
| 2003/0075172 | A1* | 4/2003 | Johnson et al. | 128/200.24 |
| 2005/0065448 | A1 | 3/2005 | Stahmann et al. | |
| 2005/0209526 | A1 | 9/2005 | Ingley, III et al. | |

(Continued)

FOREIGN PATENT DOCUMENTS

| | | |
|---|---|---|
| WO | WO 96/34604 | 11/1996 |
| WO | WO 99/30087 | 6/1999 |

OTHER PUBLICATIONS

"Pulmonary Tissue" definition from NES Integrator-Glossary accessed on Sep. 28, 2011 at www.sahservices.com/nes_provision/nes_integrator_-_glossary.*

(Continued)

*Primary Examiner* — Alton Pryor

(57) ABSTRACT

Methods, devices, and systems are provided which include an aerosol generator and a pharmaceutical composition including a membrane selective for a charged ion configured to achieve a selected pH of a pulmonary tissue in a subject. The methods, devices, or systems which include the membrane may be configured to alter selectivity for the charged ion in response to a sensed condition in the pulmonary tissue.

36 Claims, 15 Drawing Sheets

(56) References Cited

U.S. PATENT DOCUMENTS

| | | | |
|---|---|---|---|
| 2006/0122863 | A1 | 6/2006 | Gottesman et al. |
| 2007/0057077 | A1 | 3/2007 | Huang |
| 2007/0068810 | A1 | 3/2007 | Tsukashima et al. |
| 2007/0088334 | A1 | 4/2007 | Hillis et al. |
| 2007/0106138 | A1 | 5/2007 | Beiski et al. |
| 2007/0134166 | A1 | 6/2007 | Hunt et al. |
| 2007/0167843 | A1 | 7/2007 | Cho et al. |
| 2008/0000473 | A1 | 1/2008 | Stephenson et al. |
| 2008/0024323 | A1 | 1/2008 | Kadaba |
| 2008/0045156 | A1 | 2/2008 | Sakhpara |
| 2008/0138351 | A1 | 6/2008 | Dwek et al. |
| 2009/0196930 | A1 | 8/2009 | Surber et al. |
| 2010/0081954 | A1 | 4/2010 | Hyde et al. |

OTHER PUBLICATIONS

Clinical Guideline for the Diagnosis, Evaluation, and Management of Adults and Children with Asthma—2005 (accessed at www.health.state.ny.us/diseases/asthma/pdf/2005_asthma_guidelines.pdf on Oct. 2, 2011.*

Auguste et al.; "Triggered release of siRNA from poly(ethylene glycol)-protected, pH-dependent liposomes"; Journal of Controlled Release; 2008; pp. 266-274; vol. 130; Elsevier B.V.

Brabec et al.; "Conformational Changes, Plasma Membrane Penetration, and Infection by Human Rhinovirus Type 2: Role of Receptors and Low pH"; Journal of Virology; May 2003; pp. 5370-5377; vol. 77, No. 9; American Society for Microbiology.

Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

Carraro et al.; "*S*-nitrosothiols regulate cell-surface pH buffering by airway epithelial cells during the human immune response to rhinovirus"; Atherican Journal of Physiology—Lung Cellular and Molecular Physiology; May 2006; pp. L827-L832; vol. 290; American Physiological Society.

Chauhan et al.; "Air pollution and infection in respiratory illness"; British Medical Bulletin; 2003; pp. 95-112; vol. 68; The British Council 2003.

Chen et al.; "Real-time RT-PCR for H5N1 avian influenza a virus detection"; Journal of Medical Microbiology; 2007; pp. 603-607; vol. 56; SGM.

Deamer et al.; "Large Volume Liposomes by an Ether Vaporization Method"; BBA; 1976; pp. 629-634; vol. 443; Elsevier Scientific Publishing Company, Amsterdam.

Fraley et al.; "Entrapment of a bacterial plasmid in phospholipid vesicles: Potential for gene transfer"; Proceedings of the National Academy of Sciences—Cell Biology; Jul. 1979; pp. 3348-3352; vol. 76, No. 7.

Gern et al.; "Inhibition of Rhinovirus Replication In Vitro and In Vivo by Acid-Buffered Saline"; The Journal of Infectious Diseases; Apr. 15, 2007; pp. 1137-1143; vol. 195; Infectious Diseases Society of America.

Gupta et al.; "Single virus particle mass detection using microresonators with nanoscale thickness"; Applied Physics Letters; Mar. 15, 2004; pp. 1976-1978; vol. 84, No. 11; American Institute of Physics.

Hermann et al.; "Optimization of a Sampling System for Recovery and Detection of Airborne Porcine Reproductive and Respiratory Syndrome Virus and Swine Influenza Virus"; Applied and Environmental Microbiology; Jul. 2006; pp. 4811-4818; vol. 72, No. 7; American Society for Microbiology.

Hollingsworth et al.; "Ozone and Pulmonary Innate Immunity"; Proceedings of the American Thoracic Society; 2007; pp. 240-246; vol. 4.

Hope et al.; "Production of large unilamellar vesicles by a rapid extrusion procedure. Characterization of size distribution, trapped volume and ability to maintain a membrane potential"; BBA; 1985; pp. 55-65; vol. 812; Elsevier Science Publishers B.V.

Ilyushina et al.; "Contribution of H7 haemagglutinin to amantadine resistance and infectivity of influenza virus"; Journal of General Virology; 2007; pp. 1266-1274; vol. 88; SGM.

Jeon et al.; "A DNA Aptamer Prevents Influenza Infection by Blocking the Receptor Binding Region of the Viral Hemagglutinin"; The Journal of Biological Chemistry; Nov. 12, 2004; pp. 48410-48419; vol. 279, No. 46; The American Society for Biochemistry and Molecular Biology, Inc.

Kostikas et al.; "pH in Expired Breath Condensate of Patients with Inflammatory Airway Diseases"; American Journal of Respiratory and Critical Care Medicine; 2002; pp. 1364-1370; vol. 165.

Kuhrt et al.; "Virucidal Activity of Glutaric Acid and Evidence for Dual Mechanism of Action"; Antimicrobial Agents and Chemotherapy; Dec. 1984; pp. 924-927; vol. 26, No. 6; American Society for Microbiology.

Labiris et al.; "Pulmonary drug delivery. Part I: Physiological factors affecting therapeutic effectiveness of aerosolized medications"; British Journal of Clinical Pharmacology; 2003; pp. 588-599; vol. 56; Blackwell Publishing Ltd.

Labiris et al.; "Pulmonary drug delivery. Part II: The role of inhalant delivery devices and drug formulations in therapeutic effectiveness of aerosolized medications"; British Journal of Clinical Pharmacology; 2003; pp. 600-612; vol. 56; Blackwell Publishing Ltd.

Matrosovich et al.; "Human and avian influenza viruses target different cell types in cultures of human airway epithelium"; PNAS; Mar. 30, 2004; pp. 4620-4624; vol. 101, No. 13; The National Academy of Sciences of the USA.

Myatt et al.; "Airborne rhinovirus detection and effect of ultraviolet irradiation on detection by a semi-nested RT-PCR assay"; BMC Public Health; 2003; pp. 1-7; vol. 3, No. 5; Myatt et al.

Prchla et al.; "Uncoating of Human Rhinovirus Serotype 2 from Late Endosomes"; Journal of Virology; Jun. 1994; pp. 3713-3723; vol. 68, No. 6; American Society for Microbiology.

Proske et al.; "Aptamers-basic research, drug development, and clinical applications"; Applied Microbiology and Biotechnology; 2005; pp. 367-374; vol. 69; Springer-Verlag 2005.

Renneisen et al.; "Inhibition of Expression of Human Immunodeficiency Virus-1 in Vitro by Antibody-targeted Liposomes Containing Antisense RNA to the env Region"; Sep. 25, 1990; pp. 16337-16342; vol. 265, No. 27; The American Society for Biochemistry and Molecular Biology, Inc.

Rennie et al.; "Low pH gel intranasal sprays inactivate influenza viruses in vitro and protect ferrets against influenza infection"; Respiratory Research; 2007; pp. 1-7; vol. 8, No. 38; Rennie et al.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Statheropoulos et al.; "Vegetation Fire Smoke: Nature, Impacts and Policies to Reduce Negative Consequences on Humans and the Environment"; European and Mediterranean Major Hazards Agreement; May 30, 2007; pp. 1-36; Council of Europe.

Straubinger et al.; "pH-sensitive liposomes mediate cytoplasmic delivery of encapsulated macromolecules"; Federation of European Biochemical Societies; Jan. 1985; pp. 148-154; vol. 179, No. 1; Elsevier Science Publishers B.V.

Szoka, Jr. et al.; "Comparative Properties and Methods of Preparation of Lipid Vesicles (Liposomes)"; Annual Review of Biophysics and Bioengineering; 1980; pp. 467-508; vol. 9; Annual Reviews Inc.

Takeda et al.; "Influenza A Virus $M_2$ Ion Channel Activity Is Essential for Efficient Replication in Tissue Culture"; Journal of Virology; Feb. 2002; pp. 1391-1399; vol. 76, No. 3; American Society for Microbiology.

Tanaka et al.; "Acid fog and hospital visits for asthma: an epidemiological study"; European Respiratory Journal; 1998; pp. 1301-1306; vol. 11; ERS Journals Ltd 1998.

Uiprasertkul et al.; "Influenza A H5N1 Replication Sites in Humans"; Emerging Infectious Diseases; Jul. 2005; pp. 1036-1041; vol. 11, No. 7.

Vorauer-Uhl et al.; "Determination of Liposome Size Distribution by Flow Cytometry"; Cytometry; 2000; pp. 166-171; vol. 39; Wiley-Liss, Inc.

Whiteman et al.; "Human Rhinovirus Selectivity Modulates Membranous and Soluble Forms of Its Intercellular Adhesion Molecule-1 (ICAM-1) Receptor to Promote Epithelial Cell Infectivity"; The

(56) References Cited

OTHER PUBLICATIONS

Journal of Biological Chemistry; Apr. 4, 2003; pp. 11954-11961; vol. 278, No. 14; The American Society for Biochemistry and Molecular Biology, Inc.

Williams et al.; "Low density lipoprotein receptor-independent hepatic uptake of a synthetic, cholesterol-scavenging lipoprotein: Implications for the treatment of receptor-deficient atherosclerosis"; Proceedings of the National Academy of Sciences; Jan. 1988; pp. 242-246; vol. 85.

Holma, Bo; "Effects of Inhaled Acids on Airway Mucus and Its Consequences for Health"; Environmental Health Perspectives; 1989; pp. 109-113; vol. 79.

Lee et al.; "Polymer-Caged Liposomes: A pH-Responsive Delivery System with High Stability"; Department of Chemistry & the Center for Cancer Nanotechnology Excellence; pp. S1-S9; Supporting information to J. Am Chem Soc.; Dec. 12, 2007; 129(49):15096-15097; Epub Nov. 14, 2007.

Arunabh et al.; "Human Immunodeficiency Virus and Primary Pulmonary Hypertension"; Western Journal of Medicine; Dec. 1993; pp. 708-709; vol. 159, No. 6.

Beers et al.; "The Merck Manual of Diagnosis and Therapy (Seventeenth Edition)"; bearing a date of 1999; pp. 556-569 and one cover page; Section 6; Merck Research Laboratories: Division of Merck & Co., Inc.

* cited by examiner

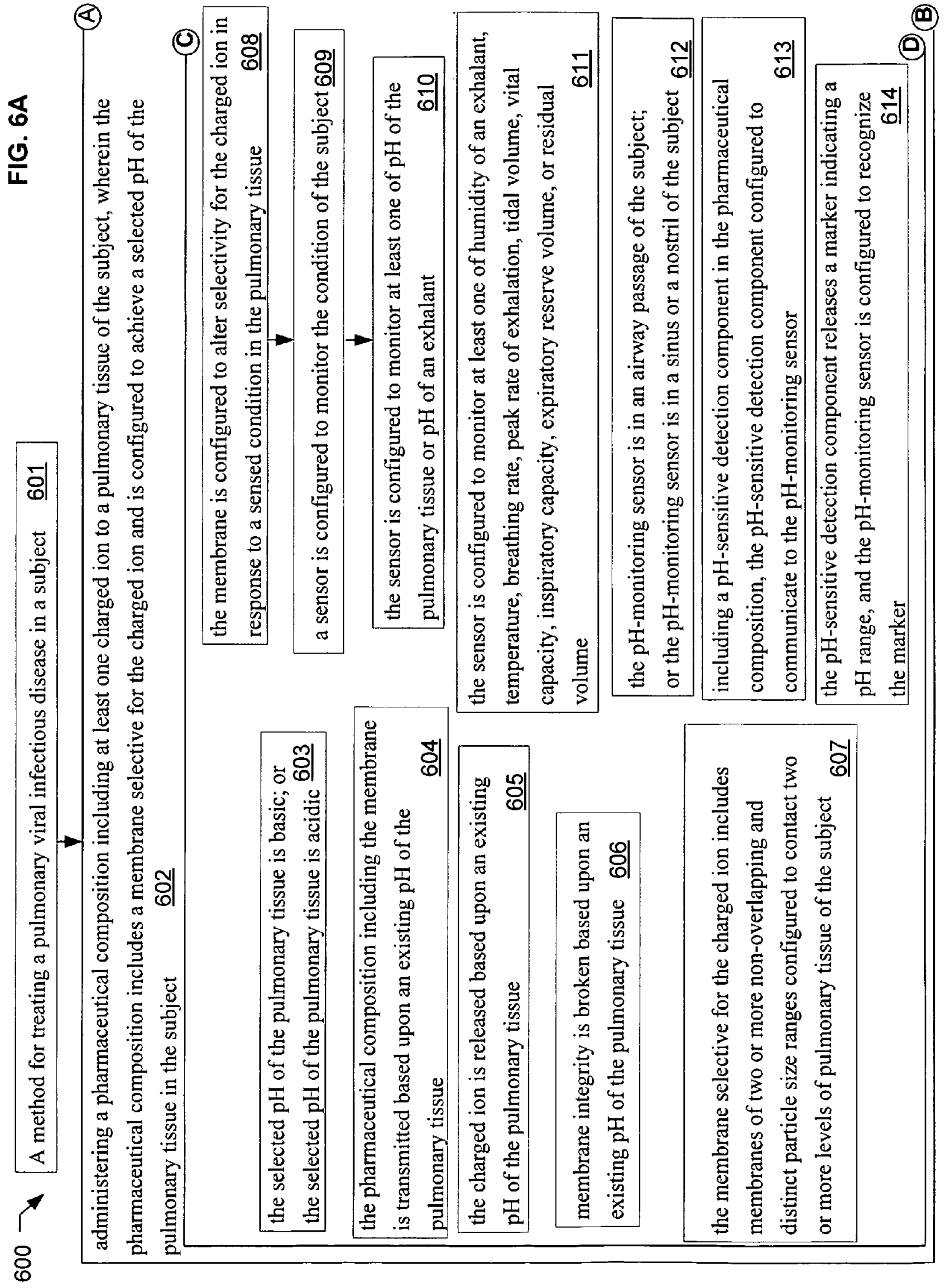
FIG. 6A
600
A method for treating a pulmonary viral infectious disease in a subject 601
administering a pharmaceutical composition including at least one charged ion to a pulmonary tissue of the subject, wherein the pharmaceutical composition includes a membrane selective for the charged ion and is configured to achieve a selected pH of the pulmonary tissue in the subject 602
A
C
the selected pH of the pulmonary tissue is basic; or the selected pH of the pulmonary tissue is acidic 603
the pharmaceutical composition including the membrane is transmitted based upon an existing pH of the pulmonary tissue 604
the charged ion is released based upon an existing pH of the pulmonary tissue 605
membrane integrity is broken based upon an existing pH of the pulmonary tissue 606
the membrane selective for the charged ion includes membranes of two or more non-overlapping and distinct particle size ranges configured to contact two or more levels of pulmonary tissue of the subject 607
the membrane is configured to alter selectivity for the charged ion in response to a sensed condition in the pulmonary tissue 608
a sensor is configured to monitor the condition of the subject 609
the sensor is configured to monitor at least one of pH of the pulmonary tissue or pH of an exhalant 610
the sensor is configured to monitor at least one of humidity of an exhalant, temperature, breathing rate, peak rate of exhalation, tidal volume, vital capacity, inspiratory capacity, expiratory reserve volume, or residual volume 611
the pH-monitoring sensor is in an airway passage of the subject; or the pH-monitoring sensor is in a sinus or a nostril of the subject 612
including a pH-sensitive detection component in the pharmaceutical composition, the pH-sensitive detection component configured to communicate to the pH-monitoring sensor 613
the pH-sensitive detection component releases a marker indicating a pH range, and the pH-monitoring sensor is configured to recognize the marker 614
D
B

700

701 A device including → 702 an aerosol generator, and a pharmaceutical composition including a membrane selective for a charged ion configured to achieve a selected pH of a pulmonary tissue in a subject

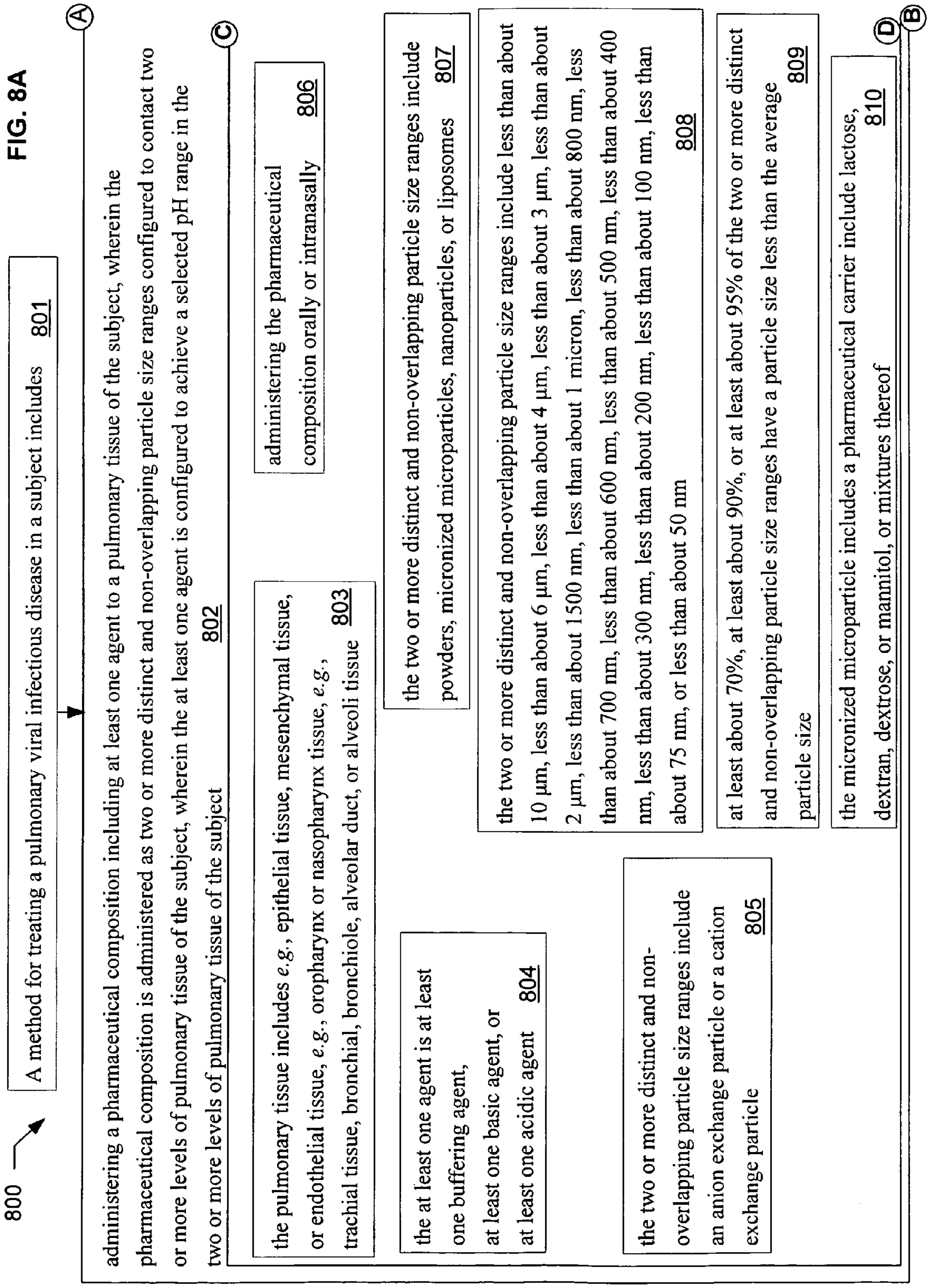
FIG. 8A
800
A method for treating a pulmonary viral infectious disease in a subject includes 801
administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject 802
A
C
the pulmonary tissue includes e.g., epithelial tissue, mesenchymal tissue, or endothelial tissue, e.g., oropharynx or nasopharynx tissue, e.g., trachial tissue, bronchial, bronchiole, alveolar duct, or alveoli tissue 803
administering the pharmaceutical composition orally or intranasally 806
the at least one agent is at least one buffering agent, at least one basic agent, or at least one acidic agent 804
the two or more distinct and non-overlapping particle size ranges include powders, micronized microparticles, nanoparticles, or liposomes 807
the two or more distinct and non-overlapping particle size ranges include an anion exchange particle or a cation exchange particle 805
the two or more distinct and non-overlapping particle size ranges include less than about 10 μm, less than about 6 μm, less than about 4 μm, less than about 3 μm, less than about 2 μm, less than about 1500 nm, less than about 1 micron, less than about 800 nm, less than about 700 nm, less than about 600 nm, less than about 500 nm, less than about 400 nm, less than about 300 nm, less than about 200 nm, less than about 100 nm, less than about 75 nm, or less than about 50 nm 808
at least about 70%, at least about 90%, or at least about 95% of the two or more distinct and non-overlapping particle size ranges have a particle size less than the average particle size 809
the micronized microparticle includes a pharmaceutical carrier include lactose, dextran, dextrose, or mannitol, or mixtures thereof 810
D
B

METHOD, DEVICE, AND SYSTEM TO CONTROL PH IN PULMONARY TISSUE OF A SUBJECT

RELATED APPLICATIONS

For purposes of the USPTO extra-statutory requirements, the present application constitutes a continuation-in-part of U.S. patent application Ser. No. 12/286,752, entitled METHOD, DEVICE, AND SYSTEM TO CONTROL PH IN PULMONARY TISSUE OF A SUBJECT, naming Roderick A. Hyde, Muriel Y. Ishikawa, Jordin T. Kare, Dennis J. Rivet, Lowell L. Wood, Jr. and Victoria Y. H. Wood as inventors, filed 30 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/286,753, entitled METHOD, COMPOSITION, AND SYSTEM TO CONTROL PH IN PULMONARY TISSUE OF A SUBJECT, naming Roderick A. Hyde, Muriel Y. Ishikawa, Jordin T. Kare, Dennis J. Rivet, Lowell L. Wood, Jr. and Victoria Y. H. Wood as inventors, filed 30 Sep. 2008, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the “Related Applications”) (e.g., claims earliest available priority dates for other than provisional patent applications or claims benefits under 35 USC §119(e) for provisional patent applications, for any and all parent, grandparent, great-grandparent, etc. applications of the Related Application(s)).

The United States Patent Office (USPTO) has published a notice to the effect that the USPTO’s computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter “Applicant”) has provided above a specific reference to the application(s) from which priority is being claimed as recited by statute. Applicant understands that the statute is unambiguous in its specific reference language and does not require either a serial number or any characterization, such as “continuation” or “continuation-in-part,” for claiming priority to U.S. patent applications. Notwithstanding the foregoing, Applicant understands that the USPTO’s computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Methods, devices, and systems are described herein which include an aerosol generator and a pharmaceutical composition including a membrane selective for a charged ion configured to achieve a selected pH of a pulmonary tissue in a subject. The methods, devices, or systems which include the membrane may be configured to alter selectivity for the charged ion in response to a sensed condition in the pulmonary tissue. The pharmaceutical composition including the membrane may be transmitted based upon an existing pH of the pulmonary tissue. The charged ion may be released based upon an existing pH of the pulmonary tissue Membrane integrity may be broken based upon an existing pH of the pulmonary tissue. The membrane selective for the charged ion may include membranes of two or more non-overlapping and distinct particle size ranges configured to contact two or more levels of pulmonary tissue of the subject. The devices or systems may further include a sensor configured to monitor the sensed condition of the pulmonary tissue from the subject. The sensor may be configured to monitor at least one of pH of the pulmonary tissue or pH of an exhalant. The devices or systems may further include a controller responsive to the sensor, the controller configured to alter the membrane selectivity for the charged ion. The controller may be configured to alter a membrane particle size range. The controller may be configured to selectively deliver one or more membrane particle size ranges. The controller may be configured to deliver one or more membrane particles of the selected pH.

Devices are described herein which include an aerosol generator and a pharmaceutical composition including a membrane selective for a charged ion configured to achieve a selected pH of a pulmonary tissue in a subject. The membrane can be configured to alter selectivity for the charged ion in response to a sensed condition in the pulmonary tissue. The pharmaceutical composition including the membrane can be transmitted based upon an existing pH of the pulmonary tissue. The charged ion may be released based upon an existing pH of the pulmonary tissue. The membrane integrity may be broken based upon an existing pH of the pulmonary tissue. The device may further include a sensor configured to monitor the sensed condition of the pulmonary tissue from the subject. The sensor can be configured to monitor at least one of pH of the pulmonary tissue or pH of an exhalant. The sensor can be configured to monitor at least one of humidity of an exhalant, temperature, breathing rate, peak rate of exhalation, tidal volume, vital capacity, inspiratory capacity, expiratory reserve volume, or residual volume. The device may further include a controller responsive to the sensor, the controller configured to alter the membrane selectivity for the charged ion. The controller can be configured to alter a membrane particle size range. The controller can be configured to selectively deliver one or more membrane particle size ranges. The controller can be configured to deliver one or more membrane particles of the selected pH. In one aspect, the monitoring sensor is in an airway passage of the subject. In a further aspect, the monitoring sensor is in a sinus or a nostril of the subject. The monitoring sensor may be integral with the device. The membrane selective for the charged ion can include membranes of two or more non-overlapping and distinct particle size ranges configured to contact two or more levels of pulmonary tissue of the subject. The two or more distinct and non-overlapping particle size ranges include, but are not limited to, powders, micronized microparticles, nanoparticles, or liposomes. The membrane selective for the charged ion includes, but is not limited to, an anion exchange particle or a cation exchange particle. The membranes selective for the charged ion have an average particle size of less than approximately 10 μm, of less than approximately 6 μm, of less than approximately 4 μm, of less than approximately 2 μm, or less than approximately 1 μm. In one aspect, the pharmaceutical composition is suitable for administration by dry powder inhalation. The membrane may be linked to a viral homing entity. The viral homing entity can bind to a surface molecule of the virus. The viral homing entity can bind to a cell or tissue of the subject. The pulmonary tissue includes, but is not limited to, an epithelial tissue, mesenchymal tissue, or endothelial tissue. The pulmonary tissue includes, but is not limited to, oropharynx, nasopharynx, tissue, trachial tissue, bronchial tissue, bronchiole tissue, alveolar duct, or alveoli tissue. The aerosol generator includes, but is not limited to, a vaporizer, nebulizer, or atomizer. The charged ion includes a cation, e.g., $H^+$, $K^+$, or $Mg^{2+}$. The charged ion includes an anion, e.g., phosphate, citrate, lactate, pyruvate, or an organic acid. The aerosol generator can be configured to administer the pharmaceutical composition to the pulmonary tissue of the subject. The pharmaceutical composition includes a buffering agent, e.g., at least one of a phosphate buffer, citrate buffer, lactate buffer, pyruvate buffer, or an organic acid buffer. The device may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The aerosol generator may be configured to administer the pharmaceutical composition orally or nasally. The aerosol generator may administer a continuous or pulsatile dose of the pharmaceutical composition. An aerosol dose of the pharmaceutical composition may be delivered directly to an individual. An aerosol dose of the pharmaceutical composition may be delivered to one or more individuals in an enclosed space. An aerosol dose of the pharmaceutical composition may be delivered through a heating, ventilation, or air conditioning system. The pharmaceutical composition may be configured to provide a timed-release of the charged ion. The pharmaceutical composition may be configured to provide a slow-absorbing form of the charged ion. The pharmaceutical composition includes, but is not limited to, a liquid or a powder.

Methods for treating a pulmonary viral infectious disease in a subject are described herein. The methods include administering a pharmaceutical composition including at least one charged ion to a pulmonary tissue of the subject, wherein the pharmaceutical composition includes a membrane selective for the charged ion and is configured to achieve a selected pH of the pulmonary tissue in the subject. The selected pH of the pulmonary tissue may be basic, or the selected pH of the pulmonary tissue may be acidic. The membrane may be configured to alter selectivity for the charged ion in response to a sensed condition in the pulmonary tissue. The pharmaceutical composition including the membrane may be transmitted based upon an existing pH of the pulmonary tissue. The charged ion may be released based upon an existing pH of the pulmonary tissue. Membrane integrity may be broken based upon an existing pH of the pulmonary tissue. The membrane selective for the charged ion includes membranes of two or more non-overlapping and distinct particle size ranges may be configured to contact two or more levels of pulmonary tissue of the subject. The method may further include a sensor configured to monitor the sensed condition of the pulmonary tissue from the subject. The sensor can be configured to monitor at least one of pH of the pulmonary tissue or pH of an exhalant. The sensor can be configured to monitor at least one of humidity of an exhalant, temperature, breathing rate, peak rate of exhalation, tidal volume, vital capacity, inspiratory capacity, expiratory reserve volume, or residual volume. The method may further include a controller responsive to the sensor, the controller configured to alter the membrane selectivity for the charged ion. The controller can be configured to alter a membrane particle size range. The controller can be configured to selectively deliver one or more membrane particle size ranges. The controller can be configured to deliver one or more membrane particles of the selected pH. In one aspect, the pH-monitoring sensor is in an airway passage of the subject. In a further aspect, the pH-monitoring sensor is in a sinus or a nostril of the subject. The pharmaceutical composition can be administered in response to a sensed environmental condition. The sensed environmental condition includes, but is not limited to, a potentially infectious environment. The pulmonary tissue includes, but is not limited to, an epithelial tissue, mesenchymal tissue, or endothelial tissue. The pulmonary tissue includes, but is not limited to, oropharynx, nasopharynx, tissue, trachial tissue, bronchial tissue, bronchiole tissue, alveolar duct, or alveoli tissue. The aerosol generator includes, but is not limited to, a vaporizer, nebulizer, or atomizer. The charged ion includes a cation, e.g., $H^+$, $K^+$, or $Mg^{2+}$. The charged ion includes an anion, e.g., phosphate, citrate, lactate, pyruvate, or an organic acid. The aerosol generator can be configured to administer the pharmaceutical composition to the pulmonary tissue of the subject. The pharmaceutical composition includes a buffering agent, e.g., at least one of a phosphate buffer, citrate buffer, lactate buffer, pyruvate buffer, or an organic acid buffer. The device may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The aerosol generator may be configured to administer the pharmaceutical composition orally or nasally. The aerosol generator may administer a continuous or pulsatile dose of the pharmaceutical composition. An aerosol dose of the pharmaceutical composition may be delivered directly to an individual. An aerosol dose of the pharmaceutical composition may be delivered to one or more individuals in an enclosed space. An aerosol dose of the pharmaceutical composition may be delivered through a heating, ventilation, or air conditioning system. The pharmaceutical composition may be configured to provide a timed-release of the charged ion. The pharmaceutical composition may be configured to provide a slow-absorbing form of the charged ion. The pharmaceutical composition includes, but is not limited to, a liquid or a powder.

Systems are described herein which include an aerosol generator, and a pharmaceutical composition including a membrane selective for a charged ion configured to achieve a selected pH of a pulmonary tissue in a subject. The membrane can be configured to alter selectivity for the charged ion in response to a sensed condition in the pulmonary tissue. The pharmaceutical composition including the membrane can be transmitted based upon an existing pH of the pulmonary tissue. The charged ion may be released based upon an existing pH of the pulmonary tissue. The membrane integrity may be broken based upon an existing pH of the pulmonary tissue. The membrane may be linked to a viral homing entity. The viral homing entity can bind to a surface molecule of the virus. The viral homing entity can bind to a cell or tissue of the subject. The system may further include a sensor configured to monitor the sensed condition of the pulmonary tissue from the subject. The sensor can be configured to monitor at least one of pH of the pulmonary tissue or pH of an exhalant. The sensor can be configured to monitor at least one of humidity of an exhalant, temperature, breathing rate, peak rate of exhalation, tidal volume, vital capacity, inspiratory capacity, expiratory reserve volume, or residual volume. The device may further include a controller responsive to the sensor, the controller configured to alter the membrane selectivity for the charged ion. The controller can be configured to alter a membrane particle size range. The controller can be configured to selectively deliver one or more membrane particle size ranges. The controller can be configured to deliver one or more membrane particles of the selected pH. In one aspect, the monitoring sensor is in an airway passage of the subject. In a further aspect, the monitoring sensor is in a sinus or a nostril of the subject. The monitoring sensor may be integral with the device. The membrane selective for the charged ion can include membranes of two or more non-overlapping and distinct particle size ranges configured to contact two or more levels of pulmonary tissue of the subject. The pharmaceutical composition can be administered in response to a sensed environmental condition. The sensed environmental condition includes, but is not limited to, a potentially infectious environment. In one aspect, the pharmaceutical composition is suitable for administration by dry powder inhalation. The pulmonary tissue includes, but is not limited to, an epithelial tissue, mesenchymal tissue, or endothelial tissue. The pulmonary tissue includes, but is not limited to, oropharynx, nasopharynx, tissue, trachial tissue, bronchial tissue, bronchiole tissue, alveolar duct, or alveoli tissue. The aerosol generator includes, but is not limited to, a vaporizer, nebulizer, or atomizer. The charged ion includes a cation, e.g., $H^+$, $K^+$, or $Mg^{2+}$. The charged ion includes an anion, e.g., phosphate, citrate, lactate, pyruvate, or an organic acid. The aerosol generator can be configured to administer the pharmaceutical composition to the pulmonary tissue of the subject. The pharmaceutical composition includes a buffering agent, e.g., at least one of a phosphate buffer, citrate buffer, lactate buffer, pyruvate buffer, or an organic acid buffer. The device may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The aerosol generator may be configured to administer the pharmaceutical composition orally or nasally. The aerosol generator may administer a continuous or pulsatile dose of the pharmaceutical composition. An aerosol dose of the pharmaceutical composition may be delivered directly to an individual. An aerosol dose of the pharmaceutical composition may be delivered to one or more individuals in an enclosed space. An aerosol dose of the pharmaceutical composition may be delivered through a heating, ventilation, or air conditioning system. The pharmaceutical composition may be configured to provide a timed-release of the charged ion. The pharmaceutical composition may be configured to provide a slow-absorbing form of the charged ion. The pharmaceutical composition includes, but is not limited to, a liquid or a powder.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 6A, 6B, and 6C depicts a logic flowchart of a method such as those depicted in FIGS. 1 and 2.

FIGS. 8A, 8B, 8C, and 8D depicts a logic flowchart of a method such as those depicted in FIGS. 1 and 2.

DETAILED DESCRIPTION

Figure 1A:
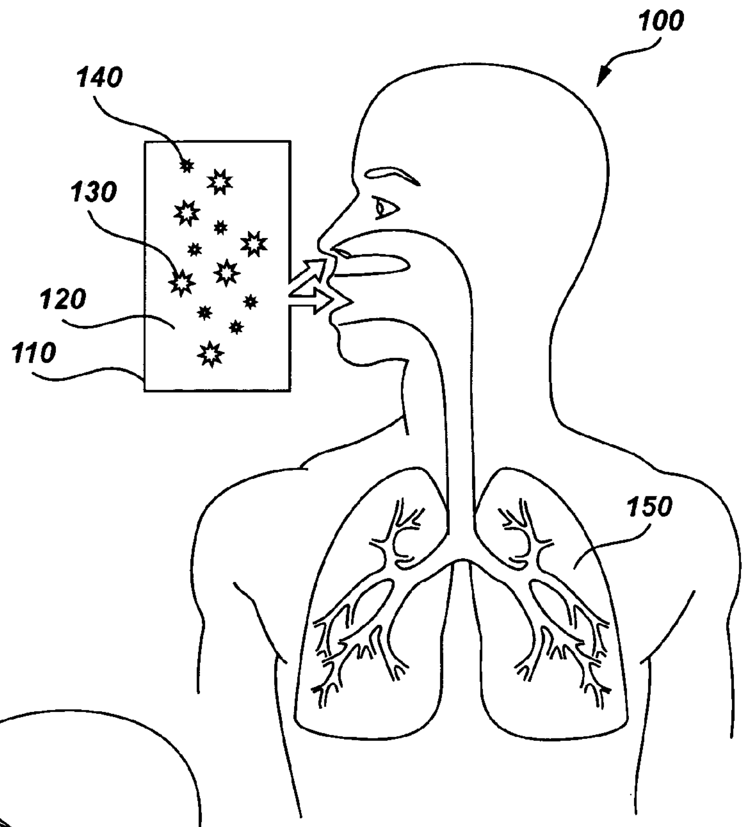
FIGS. 1A and 1B depict a diagrammatic view of one aspect of an exemplary embodiment of a method, device, or system that may serve as an illustrative environment for subject matter technologies.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Methods, devices, and systems are described herein which include an aerosol generator and a pharmaceutical composition including a membrane selective for a charged ion configured to achieve a selected pH of a pulmonary tissue in a subject. The membrane may be configured to alter selectivity for the charged ion in response to a sensed condition in the pulmonary tissue. The pharmaceutical composition including the membrane may be transmitted based upon an existing pH of the pulmonary tissue. The charged ion may be released based upon an existing pH of the pulmonary tissue Membrane integrity may be broken based upon an existing pH of the pulmonary tissue. The membrane selective for the charged ion may include membranes of two or more non-overlapping and distinct particle size ranges configured to contact two or more levels of pulmonary tissue of the subject. The devices or systems may further include a sensor configured to monitor the sensed condition of the pulmonary tissue from the subject. The sensor may be configured to monitor at least one of pH of the pulmonary tissue or pH of an exhalant. The devices or systems may further include a controller responsive to the sensor, the controller configured to alter the membrane selectivity for the charged ion. The controller may be configured to alter a membrane particle size range. The controller may be configured to selectively deliver one or more membrane particle size ranges. The controller may be configured to deliver one or more membrane particles of the selected pH.

Methods for treating a pulmonary viral infectious disease in a subject are described herein. The methods include administering a pharmaceutical composition including at least one charged ion to a pulmonary tissue of the subject, wherein the pharmaceutical composition includes a membrane selective for the charged ion and is configured to achieve a selected pH of the pulmonary tissue in the subject. The membrane may be configured to alter selectivity for the charged ion in response to a sensed condition in the pulmonary tissue. The pharmaceutical composition including the membrane may be transmitted based upon an existing pH of the pulmonary tissue. The charged ion may be released based upon an existing pH of the pulmonary tissue. Membrane integrity may be broken based upon an existing pH of the pulmonary tissue. The membrane selective for the charged ion includes membranes of two or more non-overlapping and distinct particle size ranges may be configured to contact two or more levels of pulmonary tissue of the subject.

With reference to the figures, and with reference now to FIGS. 1 through 8, depicted is one aspect of a system that may serve as an illustrative environment of and/or for subject matter technologies, for example, a method comprising receiving data including data of a physical condition affecting one or more subjects, the data informing administration of a pharmaceutical composition in response to the physical condition, wherein the pharmaceutical composition is configured to contact pulmonary tissue to treat a pulmonary disease or condition in the one or more subjects; or a method for treating a pulmonary viral infectious disease in a subject comprising administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject; or a device comprising an aerosol generator and a pharmaceutical composition including a membrane selective for a charged ion configured to achieve a selected pH of a pulmonary tissue in a subject. Accordingly, the present application first describes certain specific exemplary methods of FIGS. 1 through 8; thereafter, the present application illustrates certain specific exemplary methods. Those having skill in the art will appreciate that the specific methods described herein are intended as merely illustrative of their more general counterparts.

Figure 1B:
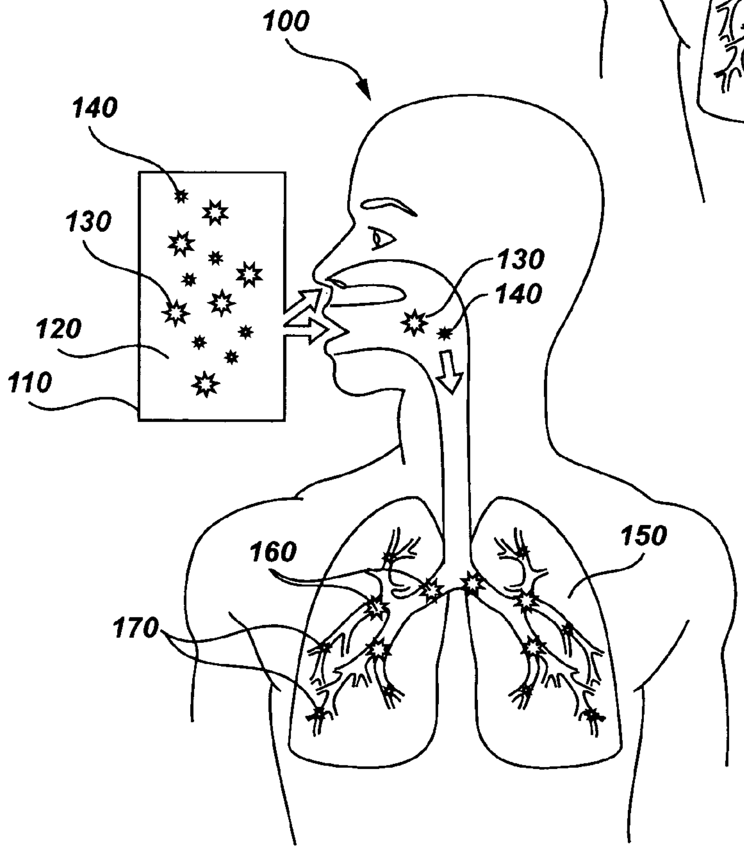

Continuing to refer to FIG. 1, depicted is a partial diagrammatic view of an illustrative embodiment of a method for treating a pulmonary viral infectious disease in a subject or a device 110 for use with the method. In FIG. 1A, a method for treating a pulmonary viral infectious disease in a subject 100 includes administering a pharmaceutical composition 120 including at least one agent 130, 140 to a pulmonary tissue of the subject, wherein the pharmaceutical composition is administered as two or more distinct and non-overlapping particle size ranges 130, 140 configured to contact two or more levels 160, 170 of pulmonary tissue 150 of the subject, In FIG. 1B, the method includes administering a pharmaceutical composition 120 including at least one agent 130, 140 to a pulmonary tissue 150 of the subject, wherein the pharmaceutical composition is administered as two or more distinct and non-overlapping particle size ranges 130, 140, wherein the at least one agent is configured to achieve a selected pH range in the two or more levels 160, 170 of pulmonary tissue 150 of the subject. The two or more distinct and non-overlapping particle size ranges 130, 140, may be configured to achieve a selected pH range in the two or more levels, for example, in the bronchus or bronchi 160 of the lungs, or further into the bronchial tree 170 towards the bronchi, bronchioles, alveolar duct, or alveoli of the lungs of the subject.

Figure 2A:
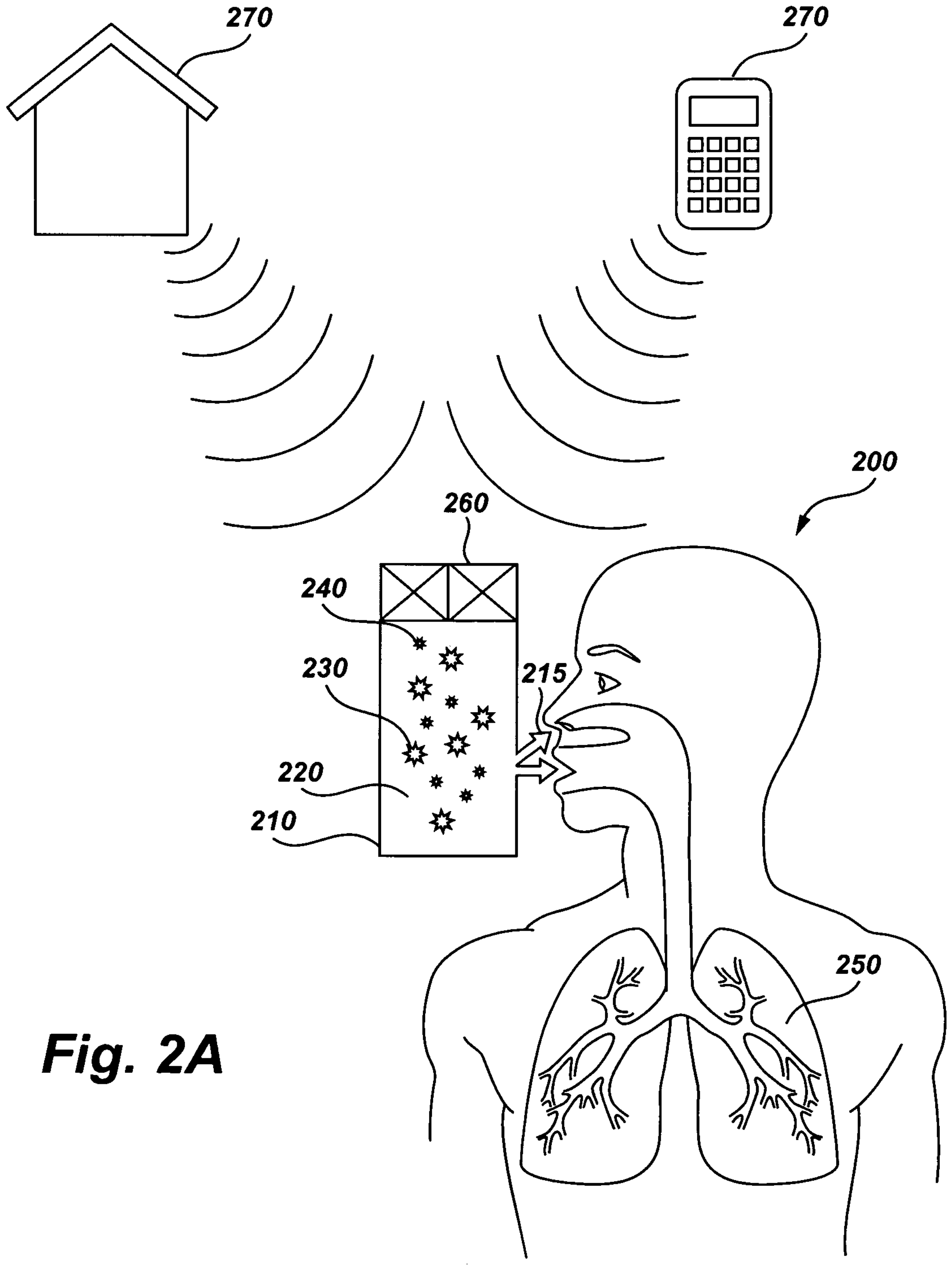
FIGS. 2A, 2B, and 2C depict a diagrammatic view of one aspect of an exemplary embodiment of a method, device, or system that may serve as an illustrative environment for subject matter technologies.
Figure 2B:
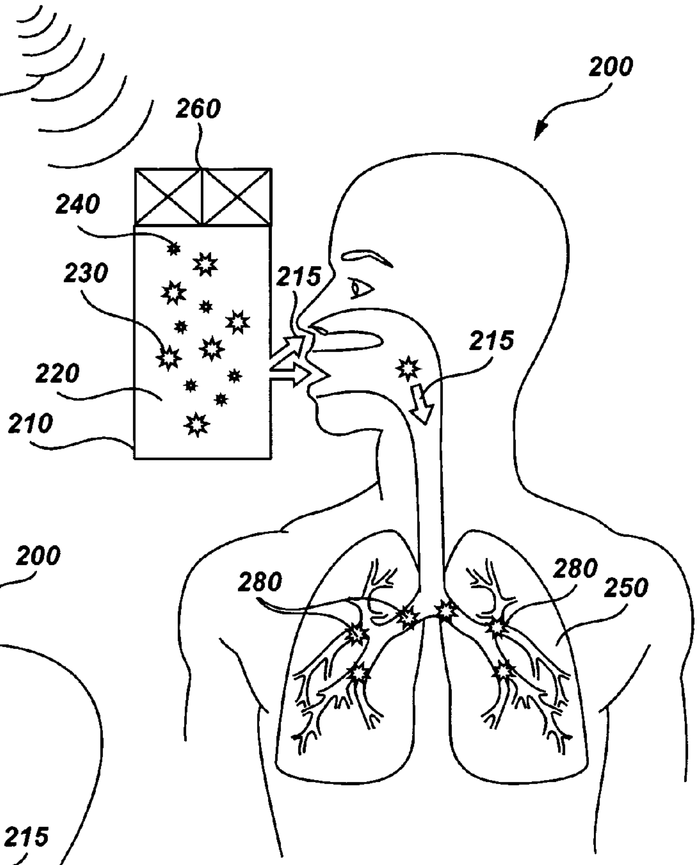
Figure 2C:
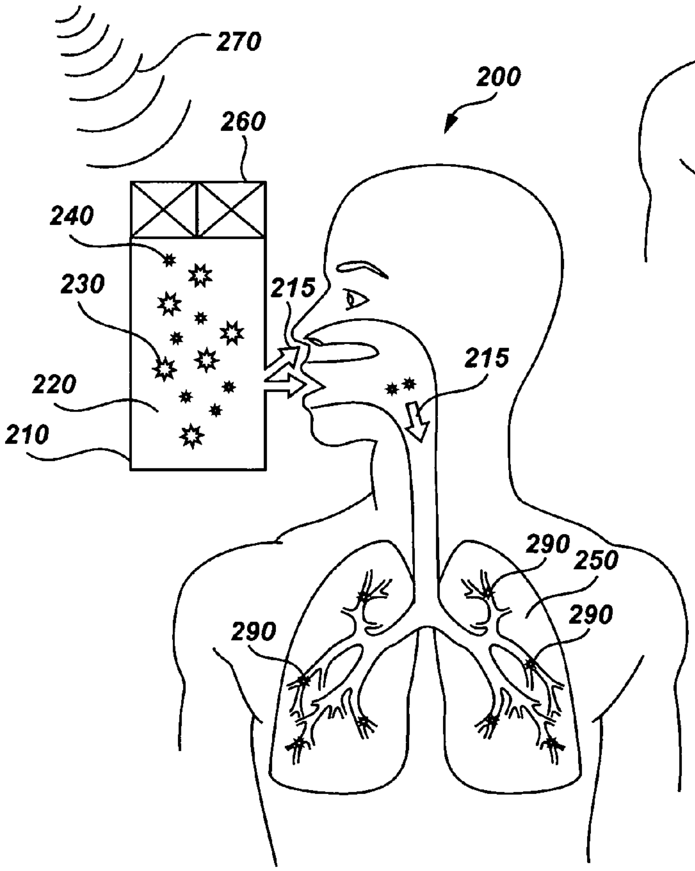

Continuing to refer to FIG. 2, FIG. 2A depicts a partial diagrammatic view 20 of an illustrative embodiment of a method comprising receiving data 260 including data 270 of a physical condition affecting one or more subjects 200, the data 270 informing administration 215 of a pharmaceutical composition 220, 230, 240 in response to the physical condition, wherein the pharmaceutical composition is configured to contact pulmonary tissue 250, 280, 290 to treat a pulmonary disease or condition in the one or more subjects 200. The system or method may include a device 210. The system or method includes providing data 270 including data of a physical condition affecting one or more subjects, the data informing administration 215 of a pharmaceutical composition in response to the physical condition, wherein the pharmaceutical composition 220, 230, 240 contacts pulmonary tissue 250 to treat a pulmonary disease or condition in the one or more subjects. In FIGS. 2B and 2C, the pharmaceutical composition 220 includes at least one agent 230, 240 and is configured to achieve a selected pH range 280, 290 of the pulmonary tissue 250 of the one or more subjects 200. Two or more distinct and non-overlapping particle size ranges 230, 240, may be configured to achieve a selected pH range in the two or more levels, for example, in the bronchus or bronchi 280 of the lungs, or further into the bronchial tree 290 towards the bronchi, bronchioles, alveolar duct, or alveoli of the lungs of the subject.

Figure 3A:
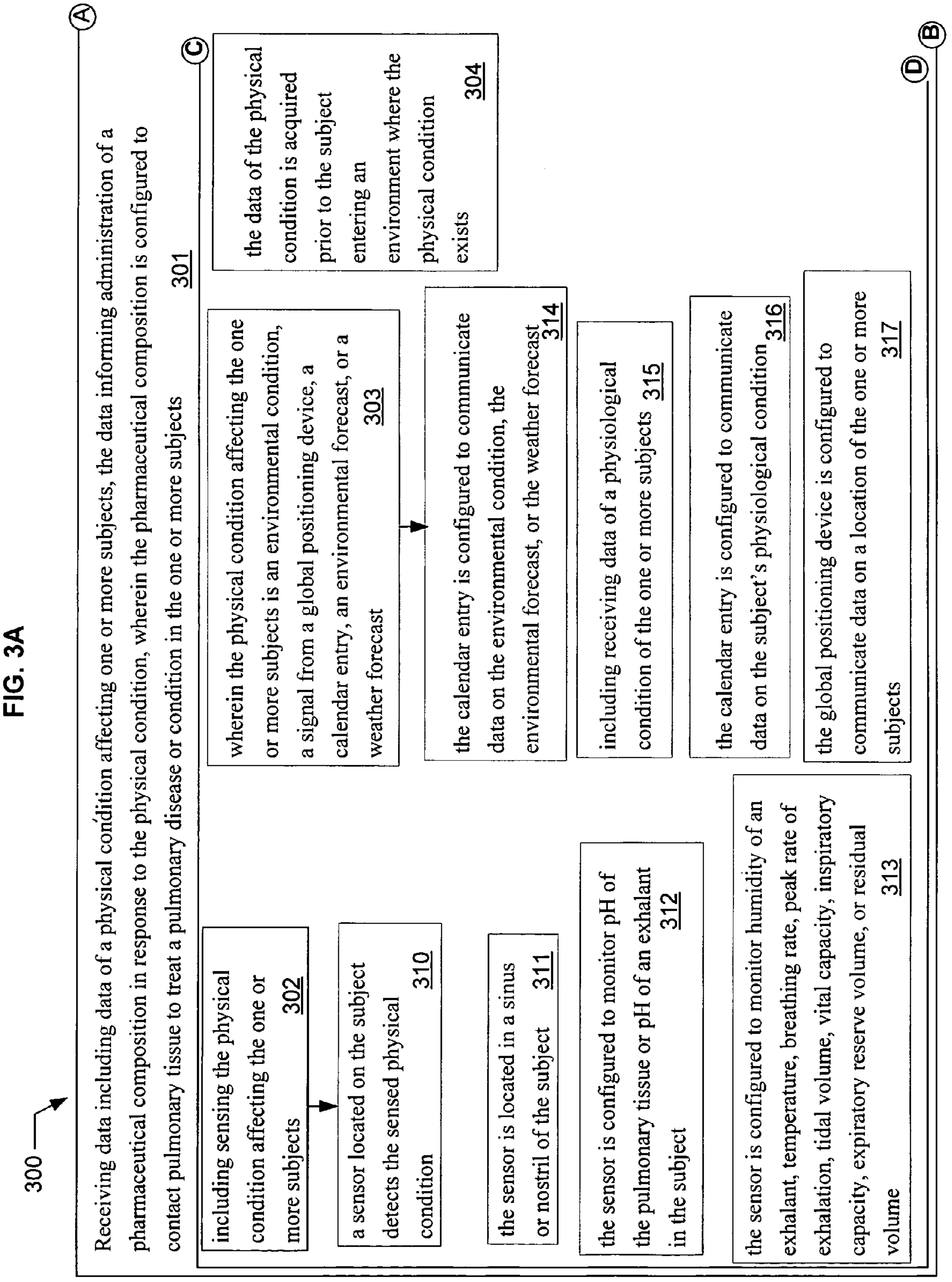
FIGS. 3A and 3B depict a logic flowchart of a method such as those depicted in FIGS. 1 and 2.
Figure 3B:
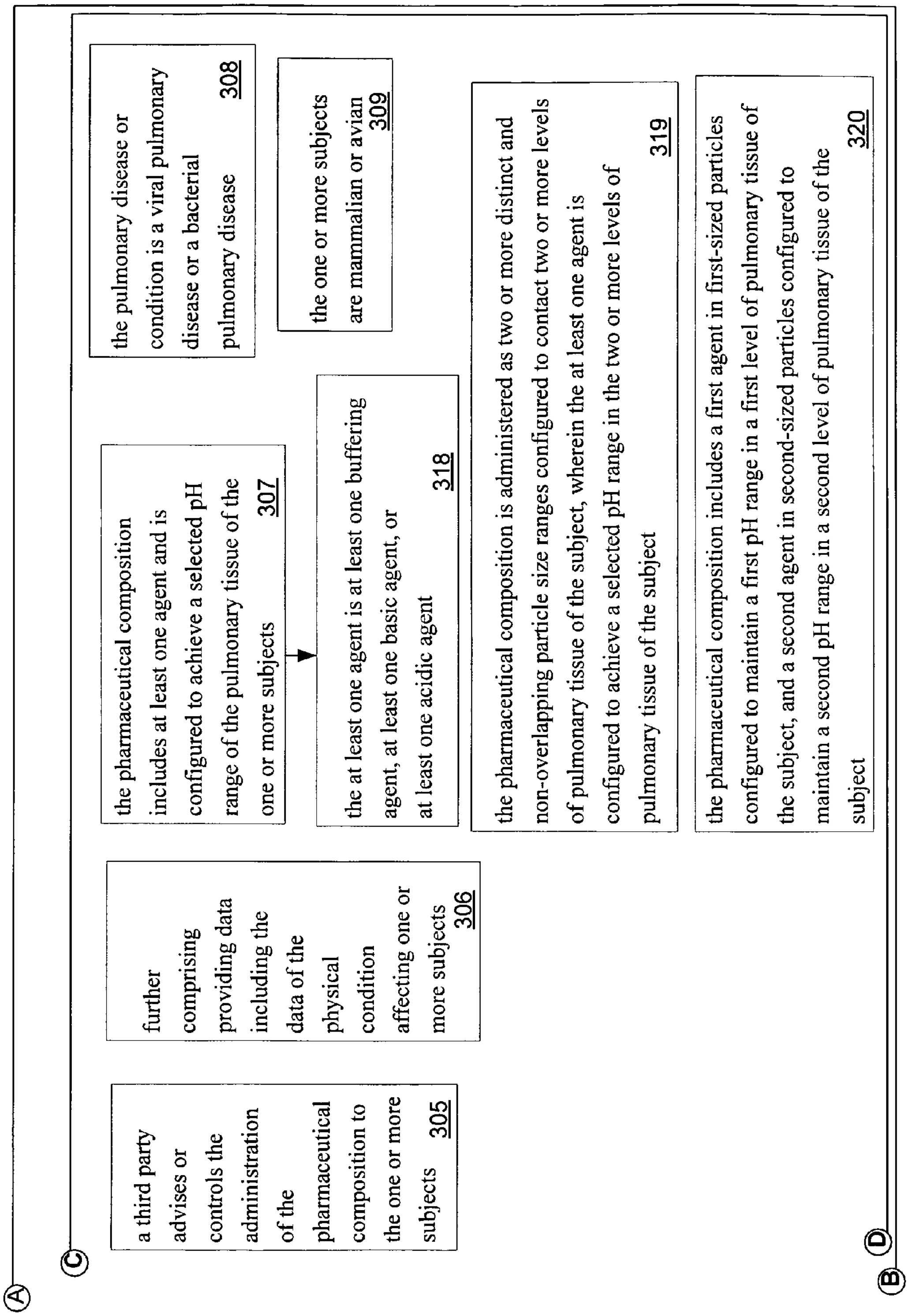

FIGS. 3A and 3B depict a logic flowchart of a method such as those depicted in FIGS. 1 and 2. FIGS. 3A and 3B illustrate an exemplary method 300 for receiving data including data of a physical condition affecting one or more subjects, the data informing administration of a pharmaceutical composition in response to the physical condition, wherein the pharmaceutical composition is configured to contact pulmonary tissue to treat a pulmonary disease or condition in the one or more subjects.

Figure 4:
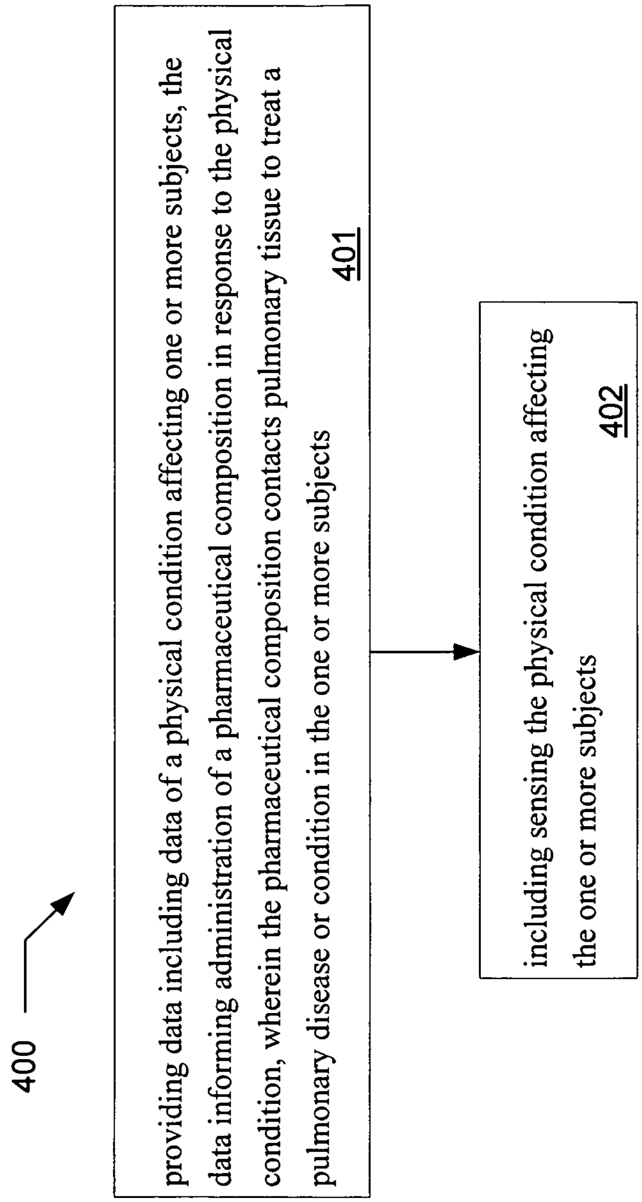
FIG. 4 depicts a logic flowchart of a method such as those depicted in FIGS. 1 and 2.

FIG. 4 depicts a logic flowchart of a method such as those depicted in FIGS. 1 and 2. FIG. 4 illustrates an exemplary method 400 including providing data including data of a physical condition affecting one or more subjects, the data informing administration of a pharmaceutical composition in response to the physical condition, wherein the pharmaceutical composition contacts pulmonary tissue to treat a pulmonary disease or condition in the one or more subjects.

Figure 5:
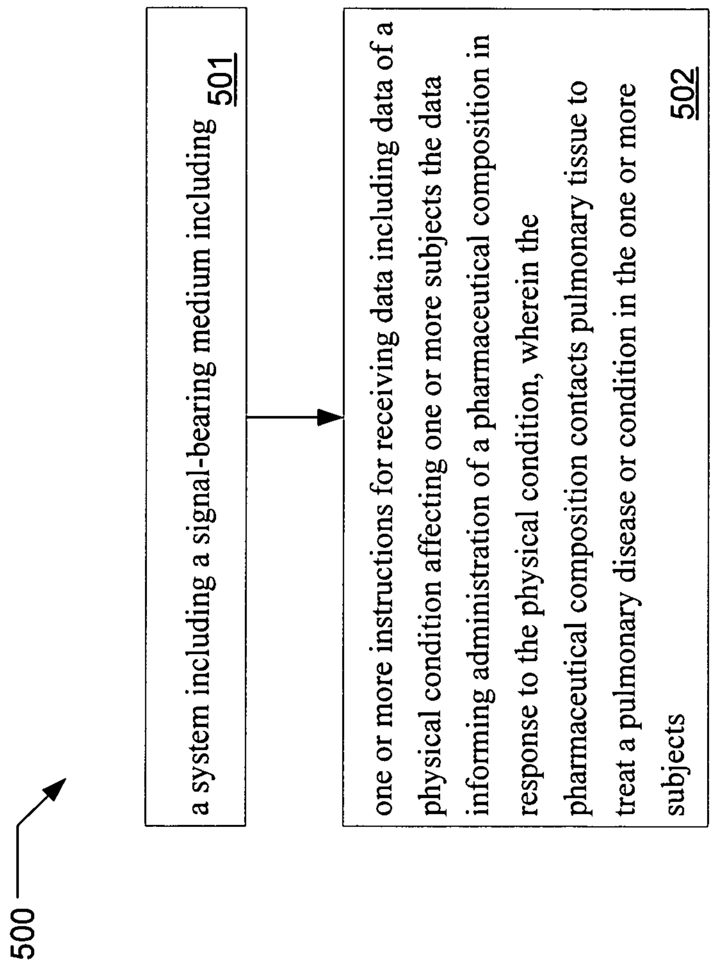
FIG. 5 depicts a logic flowchart of a device such as those depicted in FIGS. 1 and 2.

FIG. 5 depicts a logic flowchart of a device such as those depicted in FIGS. 1 and 2. FIG. 5 illustrates an exemplary device 500 including a signal-bearing medium which includes one or more instructions for receiving data including data of a physical condition affecting one or more subjects the data informing administration of a pharmaceutical composition in response to the physical condition, wherein the pharmaceutical composition contacts pulmonary tissue to treat a pulmonary disease or condition in the one or more subjects.

Figure 6B:
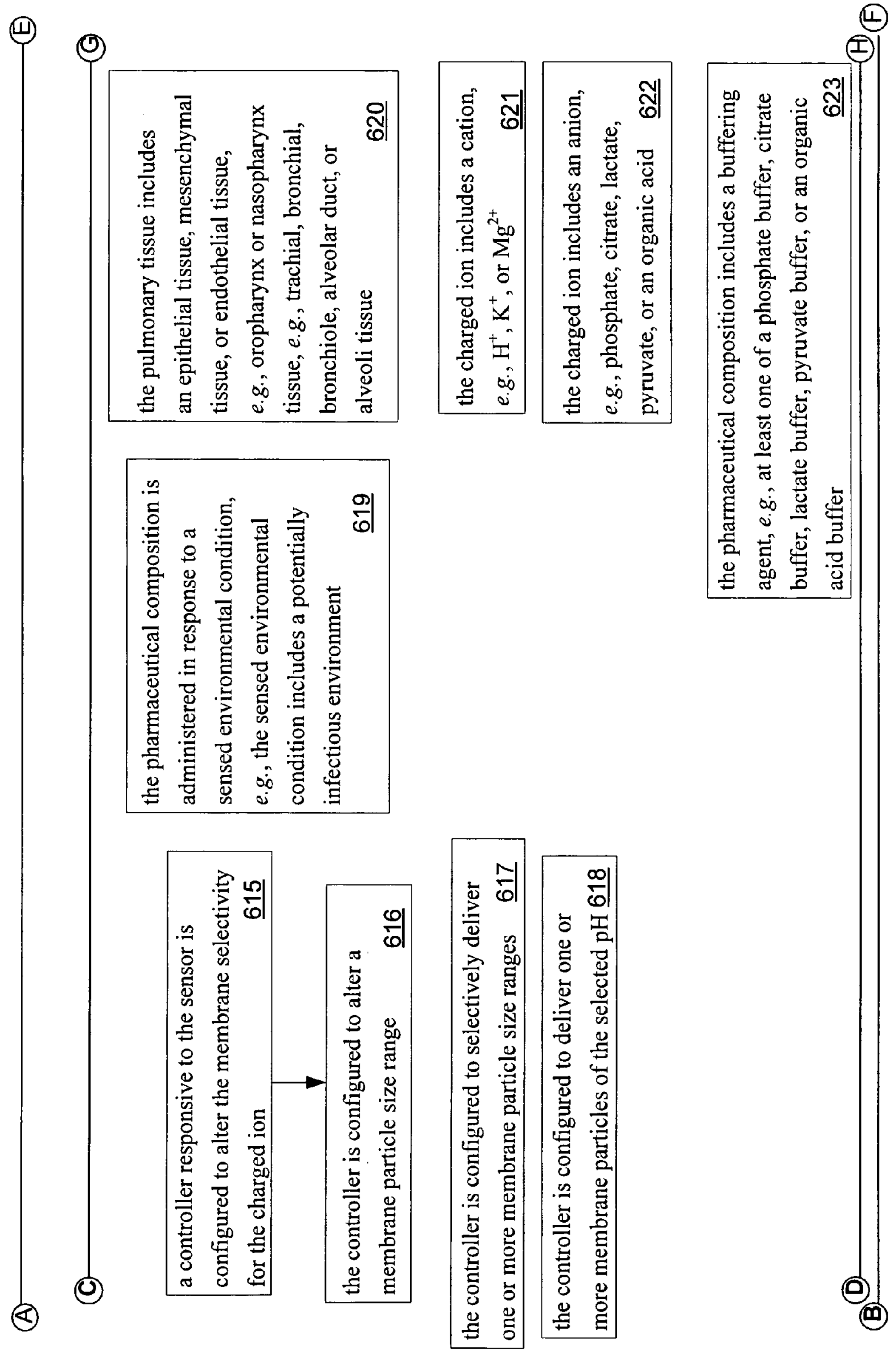
Figure 6C:
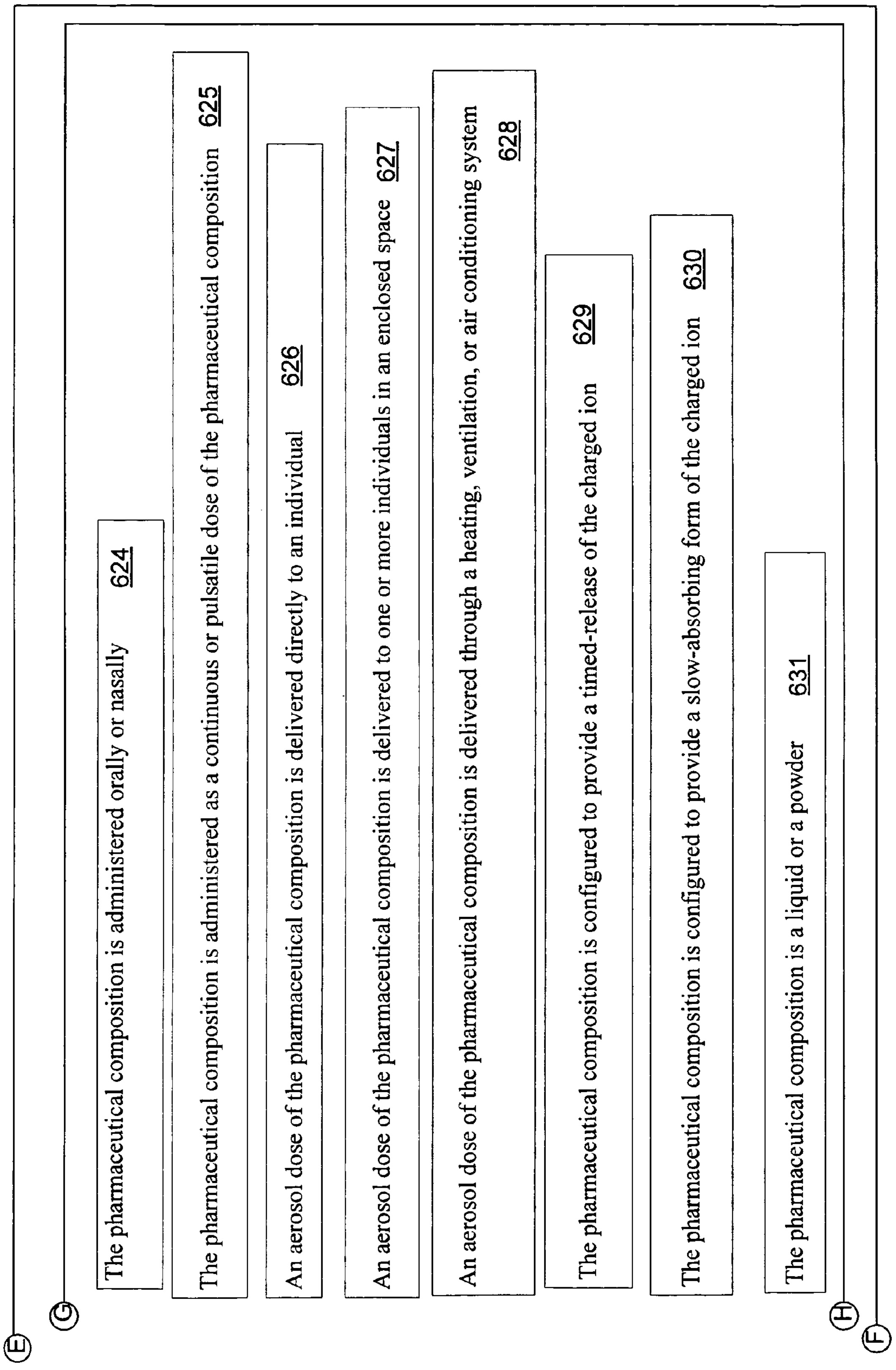

FIGS. 6A, 6B, and 6C depict a logic flowchart of a method such as those depicted in FIGS. 1 and 2. FIGS. 6A, 6B, and 6C illustrate an exemplary method 600 for treating a pulmonary viral infectious disease in a subject which includes administering a pharmaceutical composition including at least one charged ion to a pulmonary tissue of the subject, wherein the pharmaceutical composition includes a membrane selective for the charged ion and is configured to achieve a selected pH of the pulmonary tissue in the subject.

Figure 7:
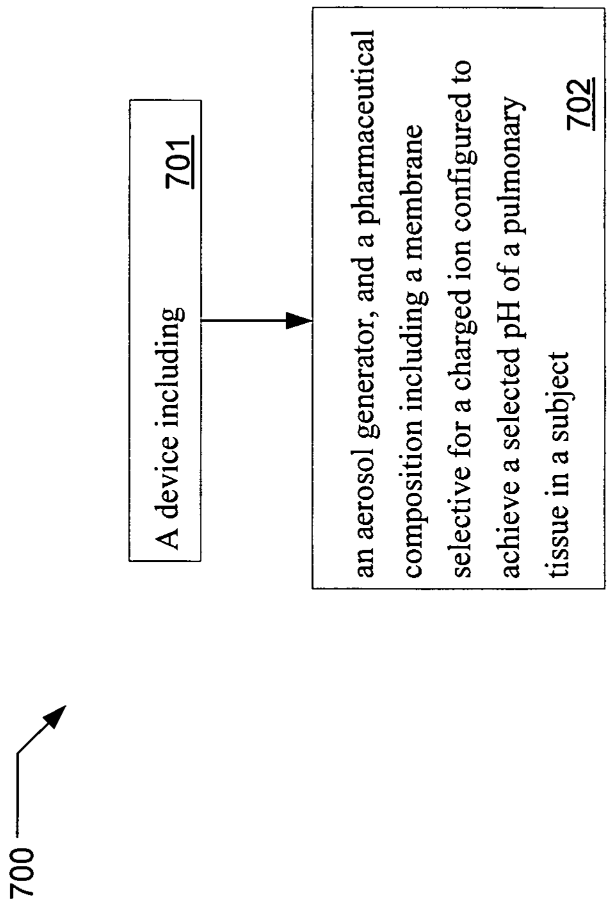
FIG. 7 depicts a logic flowchart of a device such as those depicted in FIGS. 1 and 2.
Figure 8B:
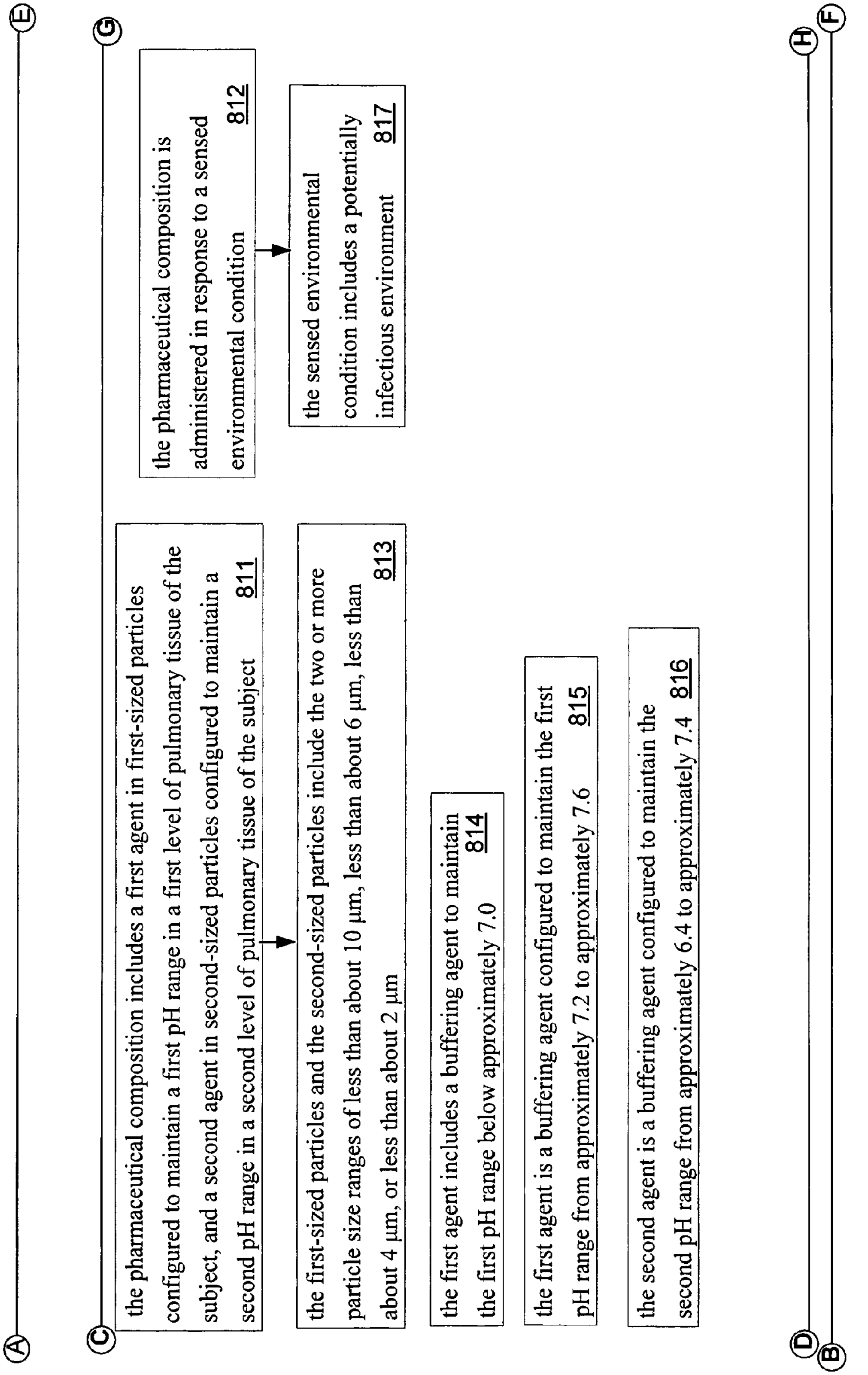
Figure 8C:
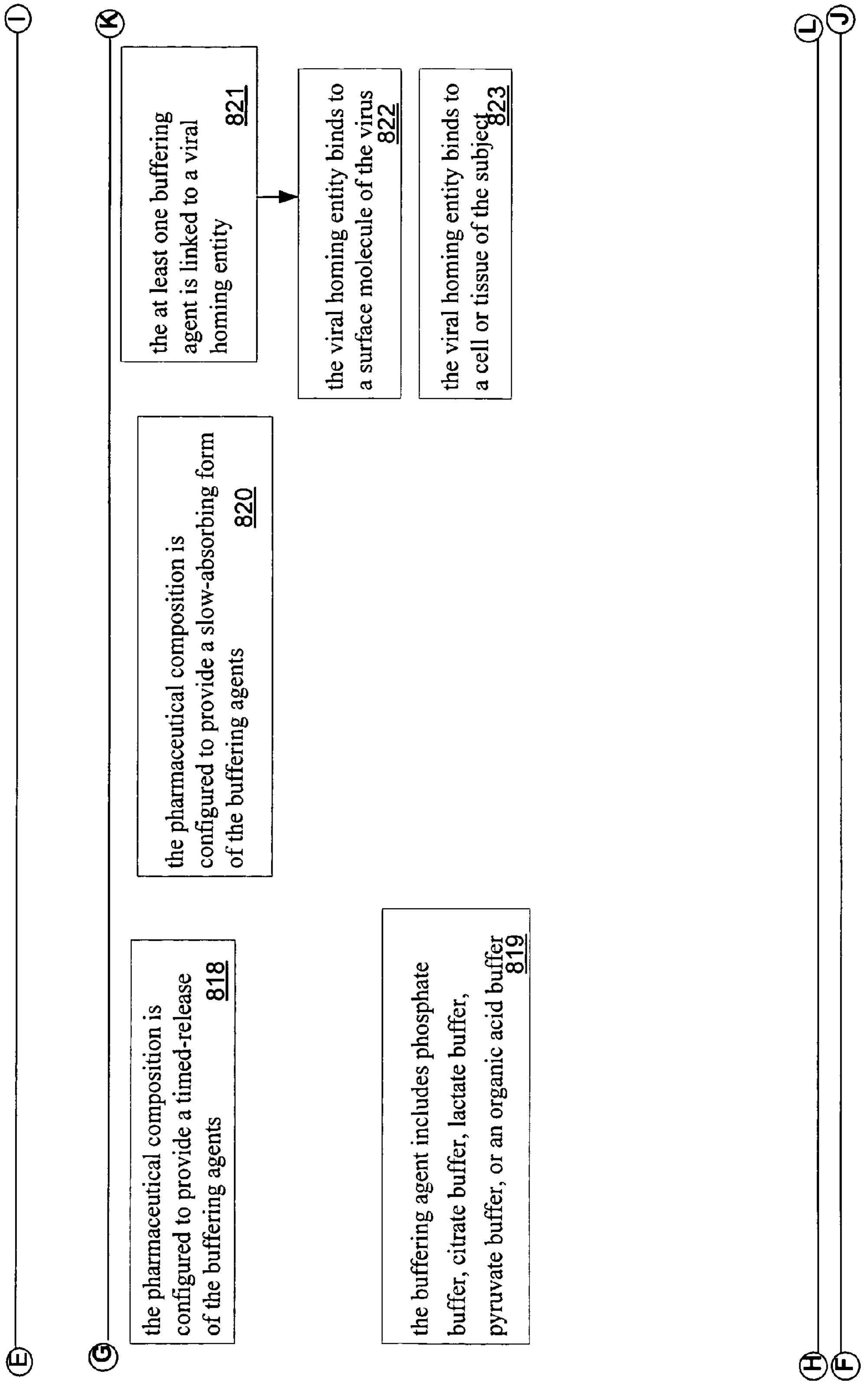
Figure 8D:
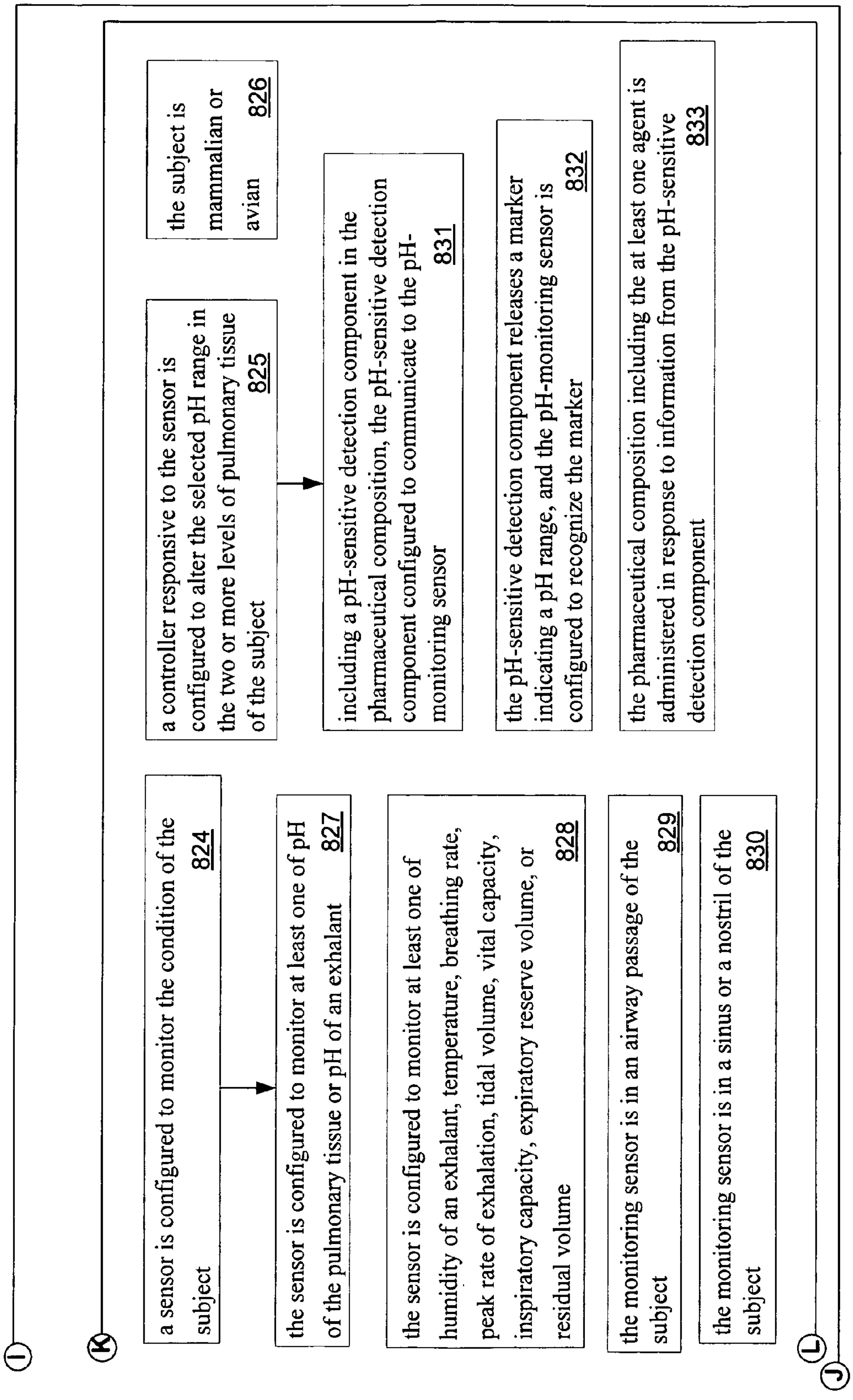

FIG. 7 depicts a logic flowchart of a device such as those depicted in FIGS. 1 and 2. FIG. 7 illustrates an exemplary device 700 including an aerosol generator, and a pharmaceutical composition including a membrane selective for a charged ion configured to achieve a selected pH of a pulmonary tissue in a subject.

FIGS. 8A, 8B, 8C, and 8D depict a logic flowchart of a method such as those depicted in FIGS. 1 and 2. FIGS. 8A, 8B, 8C, and 8D illustrate an exemplary method 800 for treating a pulmonary viral infectious disease in a subject which includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

Effects of Pulmonary pH and Pharmaceutical Composition on Viral Infection in a Subject A pulmonary condition may be prevented and/or treated using a device including an aerosol generator to administer a pharmaceutical composition including a membrane selective for a charged ion configured to achieve a selected pH of a pulmonary tissue in a subject. The normal pH of the fluid lining human airways within the pulmonary tissue ranges from about pH 6.5 to pH 7.5 (see, e.g., Tanaka, et al., *Eur. Respir. J.* 11:1301-1306, 1998, which is incorporated herein by reference). Under certain pathological conditions, the pH within the pulmonary tissue may change. Endogenous airway acidification, as assessed by abnormally low pH in expired breath condensate, is associated with pathophysiology of various inflammatory airway diseases including, but not limited to, cystic fibrosis, asthma, chronic obstructive pulmonary disease (COPD) and bronchiectasis associated with lung transplant rejection (see, e.g., Kostikas, et al., *Am. J. Respir. Crit. Care Med.* 165:1364-1370, 2002; Dupont, et al., *Am. J. Transplant.* 6:1486-1492, 2006, which are incorporated herein by reference). In subjects having asthma, the decrease in airway pH may be associated with increased mucus production, augmented inflammatory cell degranulation, bronchoconstriction, and cough characteristic of an asthma exacerbation (see, e.g., Carraro, et al., *Am. J. Physiol. Lung Cell. Mol. Physiol.* 290:L827-L832, 2006, which is incorporated herein by reference). Airway alkalinization has been contemplated for the treatment of inflammatory airway diseases (see, e.g., U.S. Patent Application 2005/0222103 A1, which is incorporated herein by reference). Modifying the pH of the pulmonary tissue with a device including an aerosol generator and a pharmaceutical composition configured to deliver a pH modifying agent may be used to prevent and/or treat a viral infection by preventing binding, fusion, and replication of the viral particles.

pH within the pulmonary tissue may also contribute to susceptibility to viral infection in terms of target cell invasion, replication within the target cell, and release from the target cell. Two examples of viruses that infect the pulmonary tissue and may be influenced by pH include the influenza viruses, associated with the flu, and human rhinoviruses, associated with the common cold. A number of other viruses induce infection within the respiratory system and may be influenced by the pH of the pulmonary tissue. These include, but are not limited to, parainfluenza virus, coronavirus, respiratory syncytial virus, adenovirus, cytomegalovirus, and hantavirus.

In general, three steps determine the early events in viral infection of a host cell: absorption to the plasma membrane by binding to specific receptors, penetration, and subsequent uncoating of the genome. Many enveloped and nonenveloped viruses enter a cell via receptor-mediated endocytosis, with membrane penetration and uncoating taking place from the endosomes. Internalization of viral particles is initiated by invagination of the plasma membrane. After pinching off, these vesicles derived from the plasma membrane reach the early endosome compartment. In early endosomes, the internalized material are either sorted into the recycling pathway or are directed via late endosomes to lysosomes for degradation. Viruses are transported to the compartment providing conditions suitable for delivery to the cytoplasm. The low pH (6.5 to 5.0) environment in endocytic and exocytic compartments has been shown to be a prerequisite for translocation into the cytoplasm.

Influenza virus is an enveloped negative-sense RNA virus. It is major public health problem worldwide and is responsible for 20,000 deaths annually in the United States alone, with the frequent emergence of new and potentially deadly strains of the virus. As with all viruses, influenza virus needs to penetrate target cells to initiate infection. An important component of influenza infectivity is the virally-associated surface glycoprotein hemagglutinin which plays a role in recognition and binding of the virus to host cells as well as fusion of the virus with the host cell membrane. Hemagglutinin consists of a receptor-binding (HA1) domain and a membrane-anchoring (HA2) domain linked by a disulfide bond. Hemagglutinin selectively binds to α-sialosides on glycoproteins and glycolipids associated with the outer surface of the target cells. Different viral hemagglutinins preferentially recognize different sialic acid-galactose linkages. For example, human influenza hemagglutinin preferentially binds alpha 2,6 linkages to galactose while the avian H5N1 influenza hemagglutinin prefers alpha 2,3 linkages to galactose. The human lung and airway epithelial cells are a prime target for influenza infection and have an abundance of alpha 2,6 linkages. The ability of hemagglutinin to bind to sialylated cell surface receptors may be pH dependent.

The influenza viral particles bound to the target cells through the interaction of hemagglutinin with sialylated cell surface receptors are taken up by the target cell through the process of endocytosis. The low pH environment of the endosomes induces a large conformational change in hemagglutinin which in turn is thought to trigger fusion between the viral membrane and the endosomal membrane. The optimal pH range for membrane fusion by hemagglutinin is between pH 5 and 5.5. The low pH environment of the endosome also activates the influenza virus M2 protein ion channel which begins to conduct protons across the viral membrane. The lowered internal virion pH is though to weaken protein-protein interactions between the viral matrix protein (M1) and the ribonucleoprotein (RNP) core. By preventing the release of M1 protein, incomplete viral uncoating occurs, and viral replication is attenuated (see, e.g., Takeda et al., *J Virol.* 76:1391-1399, 2002, which is incorporated herein by reference). Modulating the pH within the pulmonary tissue may influence influenza infectivity (see, e.g., U.S. Patent Application 2008/0000473 A1, which is incorporated herein by reference).

In some instances, lowering the pH of the pulmonary tissue with one or more acidic agents may prevent hemagglutinin binding and consequently prevent the influenza virus from binding to the target cells. It is conceivable that premature exposure of virus to low pH in the extracellular environment may induce conformational changes to spike glycoproteins on the virus surface, thereby interfering with initial binding to the target host cell (see, e.g., Rennie, et al., *Respir. Res.* 8:38, 2007, which is incorporated herein by reference).

Human rhinoviruses are the most frequent cause of upper respiratory tract infections known as the common cold. Human rhinoviruses may be inactivated by acidic solutions at or below pH 5.3 (see, e.g., Kurht, et al., *Antimicrob. Agents Chemother.* 26:924-927, which is incorporated herein by reference). Inactivation of rhinoviruses by low pH is thought to be due to conformational changes in capsid proteins at pH values of less than 6.2, which may lead to loss of the VP4 subunit of the capsid and render the virus noninfectious. Treatment of rhinovirus-infected mammalian cells with acidic solutions, e.g., citrate/phosphate buffer (pH 5.0), ascorbate (pH 5.0), or phthalate (pH 5.0), has been shown to reduce viral titer by as much as 90% (see, e.g., Gern, et al., *J. Infect. Dis.* 195:1137-1143, 2007, which is incorporated herein by reference).

Influenza viruses may also be inactivated by low pH. Influenza A Sydney/5/95 [H3N2], Influenza A Hong Kong/8/68 [H3N2] and avian reassortment virus A/Washington/897/80 X A Mallard/New York/6750/78 [H3N2] are rapidly inactivated in vitro by contact with acid buffered solutions at pH 3.5 (see, e.g., Rennie et al., *Respir. Res.* 8:38, 2007, which is incorporated herein by reference).

Modifying the pH of the pulmonary tissue with a device including an aerosol generator and a pharmaceutical composition configured to deliver a pH modifying agent may be used to prevent and/or treat a viral infection by preventing binding, fusion, and replication of the viral particles.

Therapeutic Pharmaceutical Compositions and Formulations

A device or a system including an aerosol generator and a pharmaceutical composition as provided herein may be configured to achieve a selected pH within the pulmonary tissue of a subject to treat a pulmonary condition of a subject. The pharmaceutical composition may further include a membrane selective for a charged ion. The membrane selective for a charged ion may be a membrane vesicle, e.g., a liposome, that encapsulates one or more agents configured to achieve a selected pH. The membrane vesicle that is selective for a charged ion may further be configured to release the one or more agents of the pharmaceutical composition in response to sensed pH conditions of the pulmonary tissue.

Liposomes

The pharmaceutical composition may include a membrane selective for a charged ion that is one or more lipid vesicle or liposomes. Liposomes that exhibit regulated release properties have considerable potential for drug delivery. Membrane selectivity in liposomes may provide active drug release. Drug release from liposomes may depend upon physiological conditions, e.g., pH of a pulmonary tissue. Liposomes are generally formed by placing phospholipids into an aqueous environment which spontaneously associate into multilamellar structures that function as permeability barriers. The composition of the internal compartment of the liposomes is the same as the medium in which the liposomes were formed and which makes it possible to entrap a wide variety of materials within the lipid bilayers.

The liposomes of the pharmaceutical composition may be comprised of one or more species of lipids. Suitable lipids include amphipathic lipids in which the hydrophobic portion orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palm itoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and beta-acyloxyacids, may also be used. Additionally, such amphipathic lipids can be readily mixed with other lipids, such as triglycerides and sterols. Other bilayer-forming materials that may be used include long-chain dialkyl dimethyl ammonium compounds, for example di-stearyl dimethyl ammonium compounds such as di-stearyl dimethyl ammonium chloride, di-tallow dimethyl ammonium compounds such as di-tallow dimethyl ammonium chloride and mono- and dialkyl polyoxyethylene derivatives. Either a single phospholipid or a mixture of phospholipids may be used. Sterols, for example, cholesterol or ergosterol, may be added to the liposome to increase the stability of the liposomal bilayers and lipids possessing a positive or negative change, for example, phosphatidylethanolamine, gangliosides or phosphatic acid may be used to render the appropriate charge to the liposome and to increase the size of the aqueous compartments. Mixtures of lipids may be used to render the liposomes more fluid or more rigid and to increase or decrease permeability characteristics.

The liposomes of the pharmaceutical composition may be prepared by a variety of methods including, but not limited to, hydration of lipid films, solvent injection, reverse-phase evaporation, sonication, extrusion, high pressure/homogenization, microfluidization, detergent dialysis, calcium-induced fusion of small liposome vesicles, and ether-infusion methods as described in, e.g., Szoka, et al., Ann. Rev. Biophys. Bioeng., 9:467, 1980; U.S. Pat. Nos. 4,186,183, 4,217,344, 4,235,871, 4,2619975, 4,485,054, 4,501,728, 4,774,085, 4,837,028, and 4,946,787; Deamer and Bangham, Biochim. Biophys. Acta, 443:629-634, 1976; Fraley, et al., Proc. Natl. Acad. Sci. USA, 76:3348-3352, 1979; Hope, et al., Biochim. Biophys. Acta, 812:55-65, 1985; Mayer, et al., Biochim. Biophys. Acta, 858:161-168, 1986; Williams, et al., Proc. Natl. Acad. Sci., 85:242-246, 1988; which are incorporated herein by reference. In one aspect, liposomes may be formed from a lipid film dispersing a phospholipid or mixture of lipids in a suitable container in an organic solvent such as, ether, chloroform, or tert-butanol, and removing the organic solvent by methods such as evaporation, rotary evaporation under vacuum or lyophilization with commercially available freeze-drying equipment. Dispersing the resulting lipid film of dry lipid powder in an aqueous medium, e.g., distilled water, isotonic saline or buffered solutions, will result in the formation of liposomes. The one or more agent of the pharmaceutical composition may be included in the aqueous medium during the formation of the liposomes to encapsulate the one or more agent of the pharmaceutical composition within the forming liposomes.

The size of the liposomes of the pharmaceutical composition is dependent upon the composition of the liposome, the organic solvents and the method of synthesis (see, e.g., U.S. Pat. No. 6,596,305, which is incorporated herein by reference). Ethanol injection of solubilized lipids into an aqueous medium generates liposomes of varying size. A more homogeneous population of liposomes may be generated by extruding the formed liposomes under pressure through membranes or filters with defined pore size. Alternatively, homogenization may be used to reduce the size of liposomes by repeatedly pumping a suspension of liposomes under high pressure through a small orifice or reaction chamber until a desired size distribution is achieved.

The average size of the one or more liposomes of the pharmaceutical composition may be less than about 10,000 nm, less than about 8,000 nm, less than about 5000 nm, less than about 4000 nm, less than about 3000 nm, less than about 2000 nm, less than about 1900 nm, less than about 1800 nm, less than about 1700 nm, less than about 1600, nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm.

The size of the liposomes as provided in the pharmaceutical composition may be measured using a variety of methods including but not limited to electron microscopy, light scattering, ultracentrifugation, gel filtration, high performance liquid chromatography, and flow cytometry (see, e.g., Vorauer-Uhl, et al., Cytometry 39:166-171, 2000, which is incorporated herein by reference).

Liposomes and Extended Release

Liposomes as provided in the pharmaceutical composition may comprise one or more concentrically ordered lipid bilayers and may encapsulate an aqueous phase. The liposomes are normally not leaky, but may become leaky if a hole or pore occurs in the membrane, if the membrane is dissolved or degrades, or if the membrane temperature is increased to the phase transition temperature. Current methods of drug delivery via liposomes require that the liposome carrier will ultimately become permeable and release the encapsulated drug at the target site. This can be accomplished in a passive manner wherein the liposome bilayer degrades over time through the action of various agents in the body. Every liposome composition will have a characteristic half-life in the body. By controlling the half-life of the liposome composition, the rate at which the bilayer degrades can be somewhat regulated.

In contrast to passive drug release, active drug release involves using an agent to induce a permeability change in the liposome vesicle. Liposomes that exhibit regulated release properties have considerable potential for drug delivery. Continuous interest in this area has resulted in construction of liposomes that are sensitive to temperature, light, pH and other stimuli. In some instances, the pharmaceutical composition that includes a membrane selective for a charged ion that is one or more liposomes may be further configured for timed release of its contents. The physiochemical properties of liposomes such as size, bilayer fluidity, surface charge, as well as the method of liposome preparation, affect in vivo behavior. The vesicle size and number of bilayers are key parameters in determining the residence time of liposomes. Small liposomes (≤0.1 μm), for example, are optimized by macrophages less rapidly and to a lesser extent than large liposomes (>0.1 μm) and therefore may have a longer half-life. Small liposomes also release their contents at a slower rate. The preferred size range for an individual liposome for clinical applications has been suggested to be. It should be appreciated that formulation of small liposomes for liquid aerosol or dry powder inhalation, for example, may include generating two or more particle sizes that are preferably in the range of 1-10 μm for optimal delivery to the pulmonary tissue. In one aspect, each particle may itself contain multiple smaller liposomes encapsulating the one or more agents of the pharmaceutical composition.

Liposomes as provided in the pharmaceutical composition may be further modified to modulate macrophage-dependent clearance of the liposomes from the pulmonary tissue and as such modulate residence time. The liposomes as provided in the pharmaceutical composition may include a polymer surface coating such as polyethylene glycol (PEG) which helps the liposome evade recognition and uptake by the immune system and may prolong residence in the lung.

The bilayer fluidity of the liposomes may be modified to control release of the contents of the liposomes. In general, lipids have a characteristic phase transition temperature, existing in different physical states above and below this temperature. The phase transition temperature may range from −20° C. to 90° C. and is dependent upon the length and saturation of the fatty acid side chains. Below the phase transition temperature, the lipids are in a rigid, well-ordered arrangement. Above the phase transition temperature, lipids are in a liquid-crystalline state or fluid phase. Liposomes composed of lipids with a phase transition temperature above physiological temperature (>37° C.) may be less fluid and hence less likely to leak their contents. The fluidity of the liposome bilayer at various temperatures may be used to control release of liposome contents under physiological conditions. Alternatively, the liposome membrane may be chemically modified such that an enzyme is placed as a coating on the membrane which slowly destabilizes the liposome.

The type and density of charge on the surface of the liposomes may also influence their properties. For example, negatively charged liposomes tend to aggregate less and have increased encapsulation efficiency but have increased cell-liposome interactions and may be cleared faster than neutral liposomes. Cationic liposomes may deliver their contents to cells by fusing with the cell membrane.

pH Sensitive Release of Agent from Liposomes

In a further aspect, the pharmaceutical composition may include a means for releasing the one or more agent from the two or more particle sizes based on the microenvironment of the pulmonary tissue. The pharmaceutical composition may include one or more liposome formulations in which release of the encapsulated contents of the liposome is pH-sensitive. The pharmaceutical composition may include polymer-caged liposomes in which preformed liposomes are treated with a cholesterol-functionalized poly(acrylic acid) additive, crosslinked, and become highly stable and have tunable pH-sensitive responses (see, e.g., Lee, et al., *J. Am. Chem. Soc.* 129:15096-15097, 2007, which is incorporated herein by reference). Additional examples of pH-sensitive liposomes or other micelles are further described in Auguste, et al., *J. Control Release* [Epub ahead of print], 2008; U.S. Pat. Nos. 5,786,214, 5,965,434, 6,426,086, 6,897,196, 7,229,973, which are incorporated herein by reference.

Agents Loaded in Liposomes

The liposomes as provided in the pharmaceutical composition may be loaded with one or more agents that may be used to adjust the pH within the pulmonary tract. The one or more agent may be one or more of a basic agent, an acidic agent, a buffering agent, or a combination thereof. The pharmaceutical composition may be one or more basic agent comprising a proton acceptor for raising the pH in the airways including, but not limited to, ammonia or bicarbonate. Alternatively, the pharmaceutical composition may be one or more acidic agent comprising a proton donor for lowering the pH in the airways including, but not limited to, acetic acid, ascorbic acid, citric acid, phytic acid, succinic acid, glutaric acid, phosphoric acid, or dilute hydrochloric acid, or other proton donors. The pharmaceutical composition may be one or more buffering agents including, but not limited to, sodium bicarbonate, potassium bicarbonate, phosphate buffer, citrate buffer, lactate buffer, pyruvate buffer, phthalate buffer, glycine (amino acetic acid), bicine (N,N-bis(2-hydroxyethyl) glycine), tricine (N-[tris(hydroxymethyl)methyl]glycine), CAPS (3-(cyclohexamino)-1-propanesulphonic acid, CAPSO (3-(cyclohexamino)-2-hydroxypropanesulphonic acid), 2-(cyclohexamino)-ethenesulphonic acid, BIS-TRIS propane, MOPS, HEPES, DIPSO, TAPSO, TRIZMA, HEPPSO, POPSO, EPPS, dibasic sodium phosphate, dibasic potassium phosphate, or triethanolamine.

The liposomes as provided in the pharmaceutical composition may further include one or more agents used for treating a viral infection. Examples of agents used for treating influenza include, but are not limited to, neuraminidase antagonists as exemplified by zanamivir and oseltamivir and M2 viral channel antagonists as exemplified by amantadine and rimantadine. Other antiviral drugs of the pharmaceutical composition may include, but are not limited to, acyclovir, valacyclovir, famciclovir, penciclovir, trifluridine, ganciclovir, valganciclovir, cidofovir, abacavir, didanosine, emtricitabine, lamivudine, stavudine, tenofovir, zalcitabine, zidovudine, delavirdine, efavirenz, nevirapine, atazanavir, darunavir, fosamprenavir, indinavir, lopinavir, nelfinavir, ritonavir, saquinavir, tipranavir, interferon alfa, adefovir dipivoxil, entecavir, and ribavirin.

The liposomes as provided in the pharmaceutical composition may further include one or more agents used for treating the symptoms of a viral or bacterial infection or response to allergen. The pharmaceutical composition may include one or more decongestant including, but not limited to, oxymetazoline, phenylephrine, xylometazoline, pseudoephedrine. The pharmaceutical composition may also provide an expectorant including, but not limited to, guaifenesin. The pharmaceutical composition may further provide an antihistamine including, but not limited to, carbinoxamine, dimenhydrinate, diphenhydramine, tripelennamine, hydroxyzine, cyclizine, meclizine, brompheniramine, chlorpheniramine, promethazine, cyprohetadine, fexofenadine, loratadine, and cetirizine. Formulating a pharmaceutical composition as a dry powder for inhalation may involve either micronization via jet milling, precipitation, freeze-drying or spray-drying using various excipients, such as lipids and polymers, or carrier systems such as lactose.

Pharmaceutical Composition and Particle Size

In some aspects of the method, device, or system provided herein, it may be beneficial to alter the pH, e.g., lower or raise the pH, in one level of the pulmonary tree while maintaining the pH in another level of the pulmonary tissue. Directing the pharmaceutical composition to one or more levels of the pulmonary tissue may be accomplished by varying the particle size of the one or more agents of the pharmaceutical composition. This may be dictated by where in the pulmonary tissue a particular viral infection is likely to occur. For example, human rhinoviruses commonly infect epithelial cells in the upper respiratory tract (see, e.g., Whiteman, et al., *J. Biol. Chem.* 278:11954-11961, 2003, which is incorporated herein by reference). As such, the pharmaceutical composition may be directed specifically to the upper respiratory tract, for example, for the prevention and treatment of human rhinoviruses. In some instances, similar viral strains may target host cells in different locations within the respiratory tract (see, e.g., (see, e.g., Uiprasertkul, et al., *Emerging Infectious Dis.* 11:1036-1041, 2005; Matrosovich, et al., *PNAS* 101: 4620-4624, 2004, which are incorporated herein by reference). For example, human influenza A specifically targets epithelial cells in the upper respiratory tract that express the 2,6-linked sialyl-galactosyl moieties. In contrast, avian influenza (H5N1) targets epithelial cells expressing the 2,3-linked sialyl-galactosyl moieties. These cells in humans are primarily located deep in the lower respiratory tract in ciliated epithelial cells and Type II pneumocytes. The pharmaceutical composition may be selectively directed to a level or levels of the pulmonary tissue based on the potential viral infection site, the latter of which is dependent upon which virus a subject has been exposed to or may be exposed to in the future. Directing the pharmaceutical composition to one or more levels of the pulmonary tissue may be accomplished by varying the particle size of the one or more agents of the pharmaceutical composition.

The pharmaceutical composition may be administered as two or more particles sizes of the same or different pH modifying agent for delivery to different levels of the pulmonary tissue. The two or more particle sizes may range from approximately 1 to 4 μm, approximately 5 to 10 μm, approximately 15 to 40 μm, or approximately 50 to 100 μm. The two or more particle sizes may range from approximately less than about 10 μm, less than about 6 μm, less than about 4 μm, less than about 2 μm, or less than about 1 μm. The particle size of a pharmaceutical composition is an important variable in defining the dose deposited and the distribution of the pharmaceutical composition in the pulmonary tissue (see, e.g., Labiris & Dolovich, *Br. J. Clin. Pharmacol.* 56:588-599, 2003, which is incorporated herein by reference). Fine particles more readily distribute in the peripheral airways while larger particles may deposit in the central airways or upper respiratory tract. A particle size may be defined by its mass median aerodynamic diameter (MMAD). Particles may be deposited by inertial impaction, gravitational sedimentation or diffusion depending upon their size. While deposition occurs throughout the airways, inertial impaction generally occurs in the first 10 generations of the lung where the air velocity is high and flow is turbulent. Deposition by gravitational sedimentation predominates in the last five to six generations of the airways (smaller bronchi and bronchioles) where air velocity is low. In the alveoli region, air velocity is negligible and as such particles are deposited by sedimentation and diffusion. Those particles not deposited during inhalation are exhaled.

In general, larger particles do not readily follow changes in air flow direction and tend to deposit by inertial impaction in the upper respiratory tract. For example, most particles greater than 10 μm are deposited in the oropharyngeal region with a large amount impacting on the larynx. Aerosols with MMAD of 5-10 μm are mainly deposited in the large conducting airways as well as in the oropharyngeal region. Intermediate sized particles (3-5 μm) are carried farther into the small airways of the bronchi and bronchioles, with 50% of 3 μm particles reaching the alveolar region. Particles that are less than 3 μm may behave more like gas molecules following the airflow all the way to the alveoli. However, very small particles of less the 0.5 μm, for example, may fail to be deposited in the alveoli and instead may be exhaled.

Deposition of a pharmaceutical composition in the lungs may also be controlled by the inspiratory flow rate, the tidal volume and respiratory frequency of the subject (see, e.g., Labiris & Dolovich, *Br. J. Clin. Pharmacol.* 56:600-612, 2003, which is incorporated herein by reference). Controlling the air velocity or inspiratory flow rate by slow inhalation will maximize the number of particles that reach the alveoli and minimize the number that are exhaled. For example, fast inhalations may result in reduced peripheral deposition because the aerosol is more readily deposited by inertial impaction in the conducting airway and oropharyngeal region. When aerosols are inhaled slowly, deposition by gravitational sedimentation in peripheral region is enhanced. Peripheral deposition may also be increased with an increased in tidal volume and a decrease in respiratory frequency. As such, holding one's breath after inhalation may enable better penetration of composition into periphery of lungs.

The particle size and deposition depth of the pharmaceutical composition entering the lungs is a function of the inhaler device used and the formulation of the pharmaceutical composition. Inhalers and nebulizers of different types each have the ability to generate aerosol particles of a certain size range. For liquid formulations containing soluble pharmaceutical compositions, the size of the aerosol particle is largely a function of the design and operation of the delivery device such as the nebulizer or "atomizer" that converts the liquid into a vapor or mist. For pharmaceutical compositions in powder form and for insoluble pharmaceutical compositions that are suspended or dispersed in emulsions, the particle size in the formulation of the pharmaceutical composition is an important determining factor.

The particle size and deposition depth of the pharmaceutical composition entering the lungs is a function of the formulation of the pharmaceutical composition. Ideally the formulation retains the activity of the pharmaceutical composition as well as efficiently delivers the composition to the appropriate site of action within the lungs and allows the composition to remain in the lungs long enough to have the desired pharmacological effect. Formulating a pharmaceutical composition as a dry powder for inhalation may involve, e.g., either micronization via jet milling, precipitation, freeze-drying or spray-drying using various excipients, such as lipids and polymers, or carrier systems, such as lactose or other sugars. Particles of different sizes may be generated by modifications to the methods described above.

The size of one or more particles of the pharmaceutical composition may be measured using any of an number of methods including, but not limited to, light scattering, x-ray sedimentation, electrical sensing using the Coulter principle, sieves, spectroscopy, and microscopy combined with image analysis. In one aspect, microscopy, e.g., optical microscopy, scanning electron microscopy, laser scanning microscopy, confocal microscopy or scanning probe microscopy may be combined with image analysis software to determine the size and shape of particles (see, e.g., U.S. Pat. No. 7,009,169, which is incorporated herein by reference). The Clemex Particle Size Analyzer—PS3 is an example of a commercially available instrument for measuring particle size and shape using microscopy and image analysis (from Clemex Technologies, Inc., Longueuil, Canada). Another common method for particle size determination is to use a light scattering instrument which measures the average particle size of a population of particles as well as the distribution of the particle size of the particles. When light strikes a particle, scattering (diffraction) occurs. The light scatters in all directions, but for larger particles there is relatively more scattering to the front while for smaller particles there is relatively more scattering to the sides and back. The light scattering method reports a three-dimensional (i.e., volume) equivalent sphere diameter. One example of a commonly used light scattering instrument is the Horiba LA-920 laser light diffraction instrument (from Horiba Instruments, Inc., Irvine, Calif.). The light scattering method is particularly adapted to measuring particle size and particle size distributions of the small particles in a dispersion.

One or more particles may be sized to generate a monodisperse population of particles. Particles that are dry powder polydisperse powder particles, for example, may be sized using a series of individual and or nested sieves that may further contain beads, disks and/or other non-geometric shapes that are rotated, vibrated or agitation in any of a number of directions to generate monodisperse particles (see, e.g., U.S. Pat. No. 6,267,310, and U.S. Pat. No. 6,197,835 which are incorporated herein by reference). The monodisperse population may be characterized using the particle size analysis methods described above.

Methods, Devices, or Systems for Sensing pH of Pulmonary Tissue in a Subject

The method, device, or system may include a sensor configured to monitor a condition of a subject, e.g., at least one of pH of the pulmonary tissue or pH of an exhalant of a subject. In further aspects, the sensor may be configured to monitor at least one of humidity of an exhalant, temperature, breathing rate, peak rate of exhalation, tidal volume, vital capacity, inspiratory capacity, expiratory reserve volume, or residual volume in the subject. The sensor may be part of a device, such as a hand held device. Alternatively, the sensor may be associated with a mask warn over the mouth and or nose of the subject. In some instances, the sensor may be miniaturized and temporarily or permanently incorporated into an airway passage of the subject. The sensor sends the data regarding the pH of the pulmonary tissue/exhalant of a subject to a second component of the device that may automatically administer a pharmaceutical composition to a subject. In one aspect the second component is a controller. The controller may be responsive to the sensor and configured to alter the membrane selectivity for the charged ion. Alternatively, the sensor sends the data to the subject and/or to a third party caregiver, for example, whereupon the subject and/or third party caregiver may choose to administer a pharmaceutical composition or to alter the dosage of the pharmaceutical composition.

The pulmonary pH of a subject may be monitored in the expired breath of the subject. For example, pH may be monitored in expired breath condensate (EBC). EBC consists of: (1) aerosolized particles of airway lining fluid evolved from the airway wall by turbulent airflow, that serves as seeds for substantial; and (2) water vapor condensation, which then serves to trap (3) water soluble volatile gases. The normal range of pH values of fluid lining human airways ranges from pH 6.5 to pH 7.5 (see, e.g., Tanaka, et al., *Eur. Respir. J.* 11:1301-1306, 1998, which is incorporated herein by reference). Sampling may be accomplished by having a subject breath at tidal volumes orally into a mouthpiece attached to a cold condenser (RTube, Respiratory Research Inc., Austin, Tex.; ECoScreen II, VIASYS Healthcare, Yorba Linda, Calif.). In this instance, pH may be assayed after Argon deaeration of the EBC. In addition to oral collection methods, EBC may be collected through a nasal cannula and or an endotracheal tube. Collection times may be as short as 90 seconds or over an hour to obtain sufficient EBC. Ten minutes of breathing is commonly employed. Alternatively, pulmonary pH of a subject may be monitored in real time using a miniaturized self-condensing pH sensor as described by Tsukashima, et al., in U.S. Patent Application 2007/0068810 A1, which is incorporated herein by reference.

In some instances, the pH of expired breath condensate (EBC) may be monitored by a micro-sensor using a pH sensitive ion-sensitive effect transistor (ISFET). In this instance, a metal oxide such as $SiO_2$, $Ta_2O_5$, and or $Al_2O_3$, for example, may donate or accept a proton from the solution (in this instance the breath condensate) and leave a negatively charged or a positively charged surface group, respectively, thus generating a surface potential that varies depending upon the pH of the solution (see, e.g., U.S. Pat. Nos. 6,132,893 and 6,464,940, which are incorporated herein by reference).

The sensor as provided in the method or device for monitoring the pH in the expired breath condensate of the subject may be sufficiently small to be semi-permanently or permanently located in a segment of the airway of a subject. The sensor may be incorporated into the upper respiratory tract, including, but not limited to, the nasal cavity, pharynx and or larynx. Alternatively, the sensor may be incorporated into a dental or nasal prosthesis (see, e.g., U.S. Patent Application 2007/0106138 A1, which is incorporated herein by reference) or into a piece of jewelry such as, for example, a nose or tongue piercing (see, e.g., U.S. Patent Application 2005/0209526 A1, which is incorporated herein by reference).

Alternatively, the sensor for monitoring the pH in the expired breath condensate of the subject may be incorporated into a mask or other covering of the mouth and/or nose that is worn by the subject (see, e.g., U.S. Patent Application 2007/0068810 A1, which is incorporated herein by reference). In some instances, the mask may be worn at all times, and as such may continuously and in real time measure the pH of the expired breath condensate of a subject. Alternatively, the mask may be worn temporarily to measure the pH of the expired breath condensate of a subject at any given point in time.

The method or device as provided herein may further include a sensor configured to monitor other physiological conditions of a subject such as, pH of the pulmonary tissue or pH of an exhalant of a subject. The sensor may be configured to monitor further conditions which include, but are not limited to, humidity of an exhalant, temperature, breathing rate, peak rate of exhalation, tidal volume, vital capacity, inspiratory capacity, expiratory reserve volume, or residual volume.

Sensing a Potentially Infectious Environment

In some aspects, data regarding an environmental condition is sensed by a subject or projected or forecast to be sensed by a subject and may be sent to and received by the device or measured by the device. The data regarding an environmental condition either alone or in combination with data regarding the pH of the pulmonary tissue of a subject may further inform the administration of a pharmaceutical composition to prevent or treat an infectious condition in the subject. An environmental condition may include, for example, a potentially infectious environment.

The condition of a potentially infectious environment may be directly measured by assessing the presence or absence of airborne pathogens. Airborne pathogens such as viral particles, for example, may be detected by recovering the particles in or on a collection medium (e.g., liquid, semisolid, or solid substrate), and then assaying the substrate for the presence of the targeted virus using an appropriate assay system. In one aspect, airborne viral articles may be collected using an impinger in which a converged stream of environmental air is directed onto a liquid collection medium (see, e.g., Hermann, et al., *Appl. Environ. Microbiol.* 72: 4811-4818, 2006, which is incorporated herein by reference). Other capture mediums include, but are not limited to filters, bubblers, or impactors. Real time polymerase chain reaction (RT-PCR) amplification may be used to detect and identify viral pathogens. For example, Chen, et al., describe methods for using RT-PCR to detect and identify the avian H5N1 influenza virus (Chen et al., *J. Med. Microbiol.* 56: 603-607, 2007, which is incorporated herein by reference). Similarly, airborne rhinovirus may be collected on Teflon membranes and identified and quantified by PCR (see, e.g., Myatt, et al., BMC Public Health 3:5, 2003, which is incorporated herein by reference). Alternatively, airborne pathogens may be detected using some form of microsensor. In one aspect, arrays of silicon cantilever beams may be used as microresonator sensors to detect individual virus particles (see, e.g., Gupta, et al., *Applied Physics Lett.* 84: 1976-1978, 2003, which is incorporated herein by reference).

Alternatively, the condition of a potentially infectious environment may be implied from the time of year and global location. For example, "flu" season or that portion of the year in which there are regular outbreaks of influenza infections usually occurs in the cold half of the year in each hemisphere. In the United States, for example, flu season may run from November through March of the following year. During the colder portion of the year, people remain indoors more often and as such brings people into closer contact, allowing for easier viral transmission. In addition, cold temperatures lead to drier air and may dehydrate mucus and thus prevent the body from effectively expelling virus particles. The virus itself may survive longer on surfaces in cold temperatures.

The condition of a potentially infectious environment may be communicated to a subject or group of subjects from an agency tracking viral infection in a given location. Such an agency might be, for example, a local Public Health authority, the Center for Disease Control (CDC), the World Health Organization (WHO) or similar agencies in a given location. The location may be the current location of a subject. Alternatively, the location may be the location to which the subject will be traveling to in the near future. For example, the CDC provides weekly influenza surveillance data broken down by region such as Northeast versus Pacific.

During the "flu" season, exposure to potentially infected individuals in enclosed and crowded spaces such as, for example, buses, trains, airplanes, elevators, schools, childcare, medical facility, and others, may increase the risk of contracting a viral infection. As such, the method or device may further include a global positioning system as well as a calendar of scheduled activities of a subject to predict and monitor when a subject has or will be entering a potentially infectious environment. Upon receiving data regarding the potentially infectious environment, the device may automatically administer the pharmaceutical composition including at least one agent to a pulmonary tissue of the subject. Alternatively, the device may communicate the data to the subject who may than choose to self-administer the pharmaceutical composition.

The method, device, or system may further receive data or sense data regarding other environmental conditions that may contribute to increased susceptibility to viral infection. Other environmental conditions that may contribute to increased susceptibility to viral infection include, but are not limited to, poor air quality associated with smog, forest fire, volcanic ash; allergen conditions such as pollen count, mold spores, dander; and weather conditions such as temperature, pressure, wind speed and humidity.

Pharmaceutical Composition with a Viral Homing Entity

Methods, devices, and systems including the at least one pharmaceutical composition administered to a subject may be linked to a viral homing entity. The at least one pharmaceutical composition that includes one or more liposomes configured to achieve a selected pH of a pulmonary tissue in the subject may further include one or more viral homing entity. The viral homing entity may bind to a surface molecule of the virus. The viral homing entity may bind to a viral protein or proteins associated with the outer surface of the viral particle. Alternatively, the viral homing entity may bind to a cell or tissue of a subject that is either already virally infected or is susceptible to viral infection. Pulmonary epithelial cells are susceptible to viral infection and as such the viral homing entity may recognize and bind a protein or other biomolecule associated with the surface of pulmonary epithelial cells.

The pharmaceutical composition including the viral homing entity may include, but is not limited to, at least a portion of an antibody, antibody-coated liposome, polynucleotide, polypeptide, receptor, viral plasmid, polymer, protein, toxin, lectin, or any combination thereof.

The viral homing entity may recognize and bind to a protein or proteins associated with the outer surface of the viral particles. In one aspect, the viral homing entity may recognize and bind proteins associated with surface of influenza such as, for example, hemagglutinin (HA) and neuroaminidase (NA). Hemagglutinin plays an important role in recognition and binding to host cells as well as fusion of the virus with the host cell membrane. Hemagglutinin binds to α-sialosides on the target cell surface. Different viral hemagglutinins strictly recognize the difference in sialic acid-galactose linkage. Avian virus H3 subtype binds to avian receptor Neu5Ac(α2-3)Gal stronger than to human receptor Neu5Ac (α2-6)Gal. In contrast, neuraminidase (NA), a virus surface glycoprotein of influenza A and B viruses, cleaves the a-glycosidic linkages between sialic acid and the adjacent sugar and thus destroys virus receptors on the cell surface, extracellular inhibitors, and viral glycoproteins. The NA activity is believed to be particularly important at the late stages of infection by preventing hemagglutinin (HA)-mediated self-aggregation and facilitating release of progeny virions from cells. Interaction of virions with cell-associated and soluble sialylglycoconjugates of the host is mediated by HA and NA in an antagonistic manner, which has to be carefully balanced to allow efficient virus replication.

In some aspects, the viral homing entity may recognize and bind to a protein or proteins associated with other viruses associated with pulmonary infection. For example, the viral homing entity may recognize and bind to a protein or proteins associated with rhinovirus. Examples of proteins associated with the outer surface or capsid of rhinovirus include VP1, VP2, VP3, or VP4.

A viral homing entity that recognizes and binds to a viral protein may be an antibody or fragments thereof. Antibodies or fragments thereof for use as a viral homing entity may include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, or scFv antibodies. In one aspect, antibodies to influenza hemagglutinin may be generated using standard methods. Alternatively, antibodies to influenza hemagglutinin may be available from commercial sources (from, e.g., Santa Cruz Biotechnology, Inc., Santa Cruz, Calif.; Prosci, Inc., Poway, Calif.; United States Biological, Swampscott, Mass.). Similarly, antibodies to influenza neuroaminidase may be generated using standard methods or may be available from commercial sources (from, e.g., Genway Biotech, Inc., San Diego, Calif.; ABR Affinity Bioreagents, Golden Colo. (influenza B); Prosci, Inc., Poway, Calif.; GeneTex, Inc., San Antonio, Tex. (avian influenza).

Alternatively, the viral homing entity that recognizes and binds to a viral protein may be an aptamer. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure often termed "systematic evolution of ligands by exponential enrichment" (SELEX; see, e.g., Cao, et al., *Current Proteomics* 2:31-40, 2005; Proske, et al., *Appl. Microbiol. Biotechnol.* 69:367-374, 2005, which are incorporated herein by reference). In one aspect, aptamers that recognize and bind influenza A hemagglutinin may be constructed by screening a DNA library against a all or part of recombinant hemagglutinin using the SELEX method as described by Jeon, et al., *J. Biol. Chem.* 279:48410-48419, 2004, which is incorporated herein by reference.

The viral homing entity may be a biomolecule that is all or part of biomolecule that naturally binds to a virus. In an aspect, influenza hemagglutinin naturally binds α-sialosides on the target cell surface and as such the viral homing entity may include one or more α-sialosides. Similarly, rhinovirus interacts with ICAM-1 receptors on target cells and as such the viral homing entity may include all or part of ICAM-1. The viral homing entity may be a peptide. Novel peptides that bind selective targets may be generated using phage display methodologies (see, e.g., Spear, et al., *Cancer Gene Ther.* 8:506-511, 2001, which is incorporated herein by reference).

In some aspects, the viral homing entity may be a synthetic, small molecule compound that binds to a viral protein. In an aspect, a number of small molecule antiviral agents such as oseltamivir, zanamivir and peramivir bind to and inhibit the activity of influenza neuroaminidase. As such, the viral homing entity may constitute one or more antiviral agent either alone or conjugated to a carrier protein, for example.

In a further aspect, the viral homing entity may bind to a cell or cells in the pulmonary tissue of a subject that is either already virally infected or is susceptible to viral infection such as pulmonary epithelial cells. The viral homing entity may recognize a protein that is normally expressed on epithelial cells, e.g., Epithelial Membrane Antigen (MUC-1), Epithelial Specific Antigen (ESA), Epithelium-specific Cell Surface Glycoprotein, Epithelial Sodium Channels, Surfactant Protein, to name a few. Alternatively, the viral homing entity may recognize a protein on the surface of the target cell that is upregulated in response to the viral infection. In one aspect, rhinovirus induces expression of ICAM-1 on A549 lung epithelial cells and primary bronchial epithelial cells. ICAM1 is also a possible receptor for Rhinovirus. As such, an antibody to ICAM1 might be useful as a viral homing entity that binds to cells in the subject. Antibodies to ICAM1 are readily available from commercial sources.

Formulation of a Pharmaceutical Composition

Liquid Aerosol

The pharmaceutical composition as provided herein may be formulated for inhalation administration as a liquid aerosol. In one aspect, liposomes loaded with one or more agent, e.g., one or more acidic, basic or buffering agent, may be suspended in an appropriate aqueous medium. Examples of appropriate aqueous mediums for inhalation include, but are not limited to, water, alcohols, propylene glycol, or combinations thereof.

Dry Powder

The pharmaceutical composition as provided herein may be formulated for inhalation administration as a dry powder. Formulating the pharmaceutical composition as a dry powder for inhalation may involve particle size reduction, e.g., using jet milling, controlled precipitation, sieving, freeze-drying or spray-drying. The pharmaceutical composition may be formulated in the absence of added excipients. Alternatively, the pharmaceutical composition may be formulated with added excipients. Examples of possible excipients for dry powder formulation for inhalation include, but are not limited to, lactose, dextran, mannitol, or glucose, or a combination thereof. Other additives may be included, e.g., surfactants.

Administration of a Pharmaceutical Composition

The pharmaceutical composition including a membrane selective for a charged ion configured to achieve a selected pH of a pulmonary tissue in one or more subjects may be administered by inhalation to one or more subjects using an aerosol generator. In one aspect, the system or device includes an aerosol generator which disperses the pharmaceutical composition into the air as solid or liquid particles. In some aspects, the aerosol generator may be a personal nebulizer or inhaler for direct administration of the pharmaceutical composition to an individual subject. Alternatively, the system or device may include one or more aerosol generators may be incorporated into an enclosed space such as a specialized structure specifically for this purpose, or a public space such as an elevator, bus, train or airplane cabin, and used to administer the pharmaceutical composition to one or more subjects.

The system or device including the aerosol generator may administer the pharmaceutical composition to one or more subjects in a continuous dose over a period of time. Alternatively, the aerosol generator may administer the pharmaceutical composition to one or more subjects in one or more pulsatile doses over a period of time. The period of time over which the pharmaceutical composition is administered may be dictated by data regarding an environmental condition such as continued exposure to a potentially infectious environment. Alternatively, the period of time over which the pharmaceutical composition is administered may be dictated by data regarding a physiological condition of a subject such as a response to the pharmaceutical composition as judged by an appropriate shift in the pulmonary tissue pH towards a desired pH range.

The system or device including the aerosol generator for administration of the pharmaceutical composition may be a nebulizer such as a jet nebulizer in which compressed gas (air or oxygen) passes through a narrow orifice creating an area of low pressure at the outlet of an adjacent liquid feed tube. The pharmaceutical composition in solution is drawn up from the fluid reservoir and shattered into droplets in the gas stream. Alternatively, the nebulizer may be an ultrasonic nebulizer in which a piezoelectric crystal vibrates at a high frequency and generates a fountain of liquid in the nebulizer chamber. In this aspect, the higher the frequency of vibration, the smaller the droplet size.

The system or device including the aerosol generator for administration of the pharmaceutical composition may be a metered liquid inhaler which produces a fine aerosol in the respirable range by forcing the pharmaceutical composition solution through an array of nozzles. The pattern of holes in the nozzle as well as the size and geometry of each hole may be modified to generate droplets of a desired sized. Aerosol generators of this type are exemplified by AERx (Aradigm, Hayward, Calif., USA), AeroDose (AeroGen, Sunnyvale, Calif., USA), and Respimat (Boehringer Ingelheim, Ingelheim, Germany).

The system or device including the aerosol generator for administration of the pharmaceutical composition may be a metered-dose inhaler in which the pharmaceutical composition aerosol is driven by propellants, e.g., hydrofluoroalkanes. In some aspects, the subject may manually actuate the inhaler followed by appropriate inhalation. Alternatively, the inhaler may be breath-actuated, firing in response to the subjects inspiratory effect.

The system or device including the aerosol generator for administration of the pharmaceutical composition may be a dry powder inhaler. In this aspect, an aerosol of the pharmaceutical composition is created by directing air through loose powder. Dispersion of the powder into respirable particles depends on the creation of turbulent air flow within the powder container, causing aggregates to break up into particles small enough to be carried into the lower airways, if needed. The air flow may be generated by the subject. Alternatively, a battery driven propeller or compressed air may be used to aide in aerosolizing the powdered pharmaceutical composition.

In some aspects, the pharmaceutical composition may be administered directly to a subject using an aerosol generator that is a personal nebulizer or inhaler as provided herein. Alternatively, the pharmaceutical composition may be administered to one or more subjects in a room, building or other public space. A therapeutic air vent filter screen is provided which is impregnated with a therapeutic agent for use in medicating the environment in a room (WIPO Patent WO/1999/030087, which is incorporated herein by reference). In some aspects, the pharmaceutical composition may be administered to a subject or group of subjects as a fine mist released from one or more aerosol generators into a room or other space such as an elevator, bus, train or airplane cabin. The fine mist containing the pharmaceutical composition may be administered from one or more aerosol generators through a ventilation or heating system, for example. Alternatively, the fine mist containing the pharmaceutical composition may be delivered from one or more aerosol generators situated in the space with the flow of mist optionally directed towards a given subject or group of subjects. The one or more aerosol generators may be incorporated into other objects in the room such as a computer screen or keyboard or a telephone receiver or seat back. Alternatively, the pharmaceutical composition may be administered to a subject or group of subjects in a specially designed and enclosed area. A fine mist may be released by one or more aerosol generators into a small tent, e.g., an oxygen tent.

The system or device including the aerosol generator for administration of the pharmaceutical composition may be designed to deliver two or more distinct and non-overlapping particle size ranges configured to contact two or more levels of pulmonary tissue of the subject, wherein the at least one agent is configured to achieve a selected pH range in the two or more levels of pulmonary tissue of the subject. The aerosol generator is capable of simultaneous or sequential delivery of two or more particle types. The aerosol generator may have two or more compartments with each compartment containing a distinct liposome composition loaded with a buffer within a specific pH range, for example. Liposome compositions with new pH ranges not other wise represented in the compartments may be generated by appropriate combination of two or more liposomes with differing pH ranges. In the case of a dry powder formulation, the two or more compartments may further contain particles comprised of the liposome compositions that are of varying size for deliver to two or more levels of the pulmonary tissue. In the case of a liquid formulation, the aerosol generator itself may have one or more nozzles with two or more pore sizes for generating two or more sizes of aerosolized particles for delivery to two or more levels of the pulmonary tissue. The aerosol generator is capable of administering two or more particle types differing in size, pH or both size and pH.

The system or device including the aerosol generator may be further linked to a controller that receives data regarding an environmental and or physiological condition of one or more subjects and decides which combination of pH ranges and particle sizes are appropriate for administration based on the received data. The aerosol generator administers the appropriate pharmaceutical composition based on parameters provided by the controller. In some instances, the controller may provide parameters and automatically activate the aerosol generator to deliver the appropriate pharmaceutical composition to one or more subjects. Alternatively, the controller may send information regarding the environmental and or physiological conditions and the calculated pH and size parameters to one or more subjects or a third party caregiver. The one or more subjects or a third party caregiver may then choose to administer the pharmaceutical composition. In this aspect, the controller may provide parameters to the aerosol generator which is then manually activated by the one or more subject or third party caregiver to administer the pharmaceutical composition of appropriate particle sizes and pH ranges. Alternatively, the one or more subject or third party caregiver may manually set the parameters on the aerosol generator based on information provided by the controller.

The methods and compositions are further described with reference to the following examples; however, it is to be understood that the methods, devices, and systems are not limited to such examples.

Illustrative Embodiments

Example 1

A pulmonary condition in a subject, for example, a viral infection, may be prevented and/or treated by administering a pharmaceutical composition that includes one or more membrane selective for a charged ion configured to achieve a selected pH of a pulmonary tissue in the subject. The one or more membranes selective for a charged ion may be one or more liposomes containing one or more agents configured to achieve a selected pH in a pulmonary tissue. The one or more agent may be, e.g., a buffer, an acid, or a base, or a combination thereof. The pharmaceutical composition containing one or more liposomes loaded with one or more agents may be administered as two or more distinct and non-overlapping particle size ranges configured to contact two or more levels of pulmonary tissue of the subject, wherein the at least one agent is configured to achieve a selected pH range in the two or more levels of pulmonary tissue of the subject for the prevention and treatment of a viral infection, for example, influenza virus infection. The pharmaceutical composition may be administered using one or more aerosol generators for generating a fine dispersion of liquid or solid particles. The one or more aerosol generators may be connected to one or more sensors that receives data regarding environmental and or physiological conditions and one or more controllers which provide parameters for administering a pharmaceutical composition with appropriate pH ranges and particle sizes.

The liposomes of the pharmaceutical composition may be prepared by a variety of methods including but not limited to hydration of lipid films, solvent injection, reverse-phase evaporation, sonication, extrusion, high pressure/homogenization, microfluidization, detergent dialysis, calcium-induced fusion of small liposome vesicles, and ether-infusion methods. In one aspect, liposomes may be prepared using hydration of thins films. One or more types of phospholipid and optionally other lipid components are solubilized in an organic solvent, e.g., ethanol, and placed in a round bottom flask. The solution is dried using a rotary evaporator in the presence of nitrogen gas to form a thin film. One or more agents, e.g., a buffer, an acid, or a base, or a combination thereof are added in aqueous solution with mixing to form a milky suspension containing liposomes. The one or more agent encapsulated within the liposomes may be a cation, e.g., H+, K+, or Mg+; an anion, e.g., phosphate, citrate, lactate, pyruvate, or an organic acid; a buffer, e.g., phosphate buffer, citrate buffer, lactate buffer, pyruvate buffer, or an organic acid buffer. The liposomes formed from the thin film by treatment with the aqueous solution containing one more agents may range in size from about 50 to 500 nm in size. Smaller liposomes may be formed by sonication or extrusion through membranes or filters with defined pore size.

In a further aspect, one or more liposomes in the pharmaceutical composition may be generated using solvent injection. A lipid solution containing the lipids solubilized in one or more organic solvents is injected into an aqueous solution containing the one or more pH modifying agent. The phospholipid dipalmityolphosphatidylcholine (DPPC) is solubilized in ethanol in the presence of stearylamine and cholesterol in the molar ratio 7:2:1 and injected into the aqueous solution, to form a suspension of liposomes. The homogeneity and the size distribution of the liposomes may be varied depending upon the type and amount of lipids in the ethanol solution.

The pharmaceutical composition containing one or more liposomes may be administered as two or more distinct and non-overlapping particle size ranges. The size of the particles may be dictated by the size of the liposomes. Alternatively, the size of the particles may be dictated by the formulation and or delivery of the pharmaceutical composition. For example, the liposomes of the pharmaceutical composition may be administered for inhalation using a dry powder aerosol in which freeze dried liposomes are formulated with an excipient, e.g., lactose. In this aspect, the particle size may be modulated using micronization techniques such as milling. Alternatively, liposomes of the pharmaceutical composition may be administered for inhalation using a liquid aerosol in which liposomes are suspended in an aqueous solution. The particle size may be modulated by the nozzle and pore size through which the liquid is passed to generate a fine mist for inhalation.

The pharmaceutical composition as provided herein may be delivered by inhalation to one or more subjects using an aerosol generator. In some instances, an aerosol dose of the pharmaceutical composition may be administered directly to one or more subjects using a personal aerosol generator, e.g., a nebulizer or inhaler. The aerosol dose of the pharmaceutical composition may be administered to one or more subjects using one or more aerosol generators situated in an enclosed space. The enclosed space may a specialized structure, e.g., a small tent structure similar to an oxygen tent. Alternatively, the enclosed space may be a room or other enclosed space such as an elevator, bus, train or airplane cabin. The pharmaceutical composition may be administered to one or more subjects in a building or other public space. The fine mist containing the pharmaceutical composition may be administered from one or more aerosol generators situated in the space with the flow of mist optionally directed towards a given subject or group of subjects. The one or more aerosol generator may be incorporated into other objects in the room such as a computer screen or keyboard or a telephone receiver or seat back. The fine mist containing the pharmaceutical composition may be delivered through a ventilation or heating system.

The pharmaceutical composition containing one or more liposomes may be administered by an aerosol generator as two or more distinct and non-overlapping particle size ranges configured to contact two or more levels of the pulmonary tissue and as such achieve two or more selected pH ranges in the two or more levels of the pulmonary tissue. In this manner, different pHs may be achieved in different portions of the lung. This may facilitate directed treatment of that portion of the lung that is infected by the virus while maintaining the microenvironment in other parts of the respiratory system. The aerosol generator is capable of simultaneous or sequential delivery of two or more particle types. In one aspect, the aerosol generator may have two or more compartments with each compartment containing a distinct liposome composition, e.g., loaded with a buffer within a specific pH range. Liposome compositions with new pH ranges not other wise represented in the compartments may be generated by appropriate combination of two or more liposomes with differing pH ranges. In the case of a dry powder formulation, the two or more compartments may further contain particles comprised of the liposome compositions that are of varying size for deliver to two or more levels of the pulmonary tissue. In the case of a liquid formulation, the aerosol generator itself may have one or more nozzles with two or more pore sizes for generating two or more sizes of aerosolized particles for delivery to two or more levels of the pulmonary tissue. In this aspect, the aerosol generator is capable of administering two or more particle types differing in size, or pH, or both.

The aerosol generator may be further linked to a controller that receives data regarding an environmental and or physiological condition of one or more subjects and decides which combination of pH ranges and particle sizes are appropriate for administration based on the received data. The aerosol generator administers the appropriate pharmaceutical composition based on parameters provided by the controller. In some aspects, the controller may provide parameters and automatically activate the aerosol generator to deliver the appropriate pharmaceutical composition to one or more subjects. Alternatively, the controller may send information regarding the environmental and or physiological conditions and the calculated pH and size parameters to one or more subjects or a third party caregiver. The one or more subjects or a third party caregiver may then choose to administer the pharmaceutical composition. In this aspect, the controller may provide parameters to the aerosol generator which is then manually activated by the one or more subjects or third party caregiver to provide instructions to administer the pharmaceutical composition of appropriate particle sizes and pH ranges. The one or more subject or third party caregiver may manually set the parameters on the aerosol generator based on information provided by the controller.

Example 2

A pulmonary condition in a subject, for example, a viral infection, may be prevented and/or treated by administering a pharmaceutical composition that includes one or more membrane selective for a charged ion configured to achieve a selected pH of a pulmonary tissue in the subject. The pulmonary condition may be based on sensing data with regard to a physiological condition of the subject, for example, the current pH of the pulmonary tissue. The one or more membrane selective for a charged ion may be one or more liposomes generated as provided herein and loaded with one or more buffering agent to achieve a selected pH in the pulmonary tissue in the subject. The current pH of the pulmonary tissue of a subject may be monitored using one or more sensors. The data regarding the current pH of a subject is collected by the sensors and by one or more controller. An assessment is made as to whether the current pH falls inside or outside the expected norm. As appropriate, the controller may direct the aerosol generator to automatically administer the pharmaceutical composition in response to the current pH of the pulmonary tissue. Alternatively, the data regarding the current pH of the pulmonary tissue may be conveyed to a subject and/or a third party care giver and a decision is made as to whether to administer the pharmaceutical composition to the one or more subjects. The pharmaceutical composition containing one or more liposomes is administered as two or more distinct and non-overlapping particle size ranges configured to contact two or more levels of pulmonary tissue of the subject, wherein the at least one agent is configured to achieve a selected pH range in the two or more levels of pulmonary tissue of the subject. For example, the first particle type of the pharmaceutical composition includes liposomes containing one or more agents at a basic pH or in a buffer that achieves a pH of greater than 7.0 in one portion of the respiratory tract. The second particle type of the pharmaceutical composition includes liposomes loaded with a buffer, or acid, or base, or a combination thereof to achieve a pH ranging from about 6.5 to 7.5 in a second portion of the respiratory tract of the subject.

The method or device includes one or more sensors that are configured to monitor a physiological condition of the subject, e.g., the pulmonary pH of the subject. The pulmonary pH of a subject may be measured in the expired breath condensate, which consists, in part, of aerosolized particles from the airway lining fluid, water vapor condensation, and water soluble volatile gases. The one or more sensors are configured to monitor the pH of the expired breath condensate as an indicator of the pH of the pulmonary tissue. The one or more sensors may be further configured to monitor at least one of humidity of an exhalant, temperature, breathing rate, peak rate of exhalation, tidal volume, vital capacity, inspiratory capacity, expiratory reserve volume, or residual volume.

The one or more sensors in the method or device for monitoring pH in the expired breath condensate may be sufficiently small to be semi-permanently located in a segment of the airway of a subject. Alternatively, the sensors may be incorporated into a dental or nasal prosthesis or into a piece of jewelry, e.g., a nose or tongue piercing. Alternatively, the sensors for monitoring pH may be incorporated into a mask or other covering of the mouth and/or nose that is worn by the subject. The mask may be worn at all times, and will monitor expired breath condensate of a subject continuously and in real time. Alternatively, the mask may be worn temporarily to monitor a subject's expired breath condensate at any given point in time.

The liposomes of the pharmaceutical composition may be administered automatically in response to the sensed data with regard to the current pH of the pulmonary tissue of a subject. Alternatively, the liposomes of the pharmaceutical composition may be self-administered by the one or more subjects in response to the sensed data regarding the current pH of the pulmonary tissue of the subjects. The pharmaceutical composition may be administered as two or more distinct and non-overlapping particle size ranges configured to contact two or more levels of the pulmonary tissue and as such achieve two or more selected pH ranges in the two or more levels of the pulmonary tissue. The particle sizes and pH ranges selected are dependent upon the type of virus that has been encountered or is expected to be encountered and the relative location of the infection of that virus within the respiratory tract as described herein. For example, human influenza A preferentially infects epithelial cells expressing 2-6-linked sialyl-galactosyl moieties which are prominent in tracheal and bronchial epithelial cells. The first particle type of the composition may include one or more agents that is basic in pH or is a buffer that achieves a pH of greater than 7.0 and is sized by milling, formulation or aerosolization to specifically deposit within regions of the upper airway, trachea and bronchus with a diameter, e.g., of about 3 to 6 μm. In contrast, the second particle type of the composition achieves a pH ranging from 6.4 to 7.4 and is sized by milling, formulation, or aerosolization to a smaller diameter that enables specific deposit within regions of the lower airway such as, for example, the bronchioles and alveoli with a diameter, e.g., of about 1 to 2 μm, to maintain a normal pH level.

Example 3

A method, composition, or device is provided for administering a pharmaceutical composition including at least one agent to a pulmonary tissue of a subject to modify the pH of the pulmonary tissue as a means of preventing or treating a viral infection in the subject. The pharmaceutical composition may include one or more membranes selective for a charged ion configured to achieve a selected pH in a pulmonary tissue in the subject. The one or more membranes selective for a charged ion may be one or more liposomes generated as provided herein and loaded with one or more buffering agents to achieve a selected pH. The one or more buffering agents in the one or more liposomes may be selectively released from the liposomes in response to a condition within the microenvironment of the pulmonary tissue, for example, the pH of the pulmonary fluid or pulmonary tissue of the subject. The pharmaceutical composition may include one or more pH-sensitive liposomes configured to release one or more buffering agents in response to the local pH within the pulmonary tissue. The pharmaceutical composition containing one or more pH-sensitive liposomes may further be administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

Example 4

A pulmonary condition in a subject, such as a viral infection, may be prevented and/or treated by administering a pharmaceutical composition that includes one or more membranes selective for a charged ion and configured to achieve a selected pH of a pulmonary tissue in the subject. Administering the pharmaceutical composition is based on receiving and/or sensing data regarding an environmental condition, for example, a potentially infectious environment. The one or more membranes selective for a charged ion may be one or more liposomes generated as described herein and loaded with one or more buffering agent to achieve a selected pH in a pulmonary tissue in the subject. The potentially infectious environment may be determined based on direct measurement, inferred based on time and location, and/or provided based on data from one or more agencies involved in pathogen surveillance. The data regarding the potentially infectious environment may be acquired prior to the subject entering that environment. In response to a potentially infectious environment, the pharmaceutical composition may be self-administered or automatically administered to the subject. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

The potentially infectious environment may be determined based on direct measurement. Airborne pathogens such as viral particles may be detected by recovering the particles in or on a collection medium (liquid, semisolid, or solid substrate, for example) using, e.g., an impinger, filters, bubblers, or impactors, and then assaying the substrate for the presence of the targeted virus using an appropriate assay system. Real time polymerase chain reaction (RT-PCR) amplification may be used to determine the presence and identity of viruses. In one aspect, Chen, et al., describe using real-time PCR to detect the avian H5N1 influenza virus (Chen et al., *J. Med. Microbiol.* 56:603-607, 2007). Alternatively, airborne pathogens may be detected using some form of microsensor.

In a further aspect, potentially infectious environment may be inferred from the time of year and global location. For example, "flu" season or that portion of the year in which there are regular outbreaks of influenza infections usually occurs in the cold half of the year in each hemisphere. Data regarding a potentially infectious environment may be received by the subject from an agency tracking viral infection in a given location. Such an agency might be, for example, a local Public Health authority, the Center for Disease Control (CDC), the World Health Organization (WHO) or similar agencies in a given location. Both the CDC and WHO actively tract outbreaks of avian H5N1 influenza. The location of the potentially infectious environment may be the current location of the subject. Alternatively, the location of the potentially infectious environment may be a location or locations to which the subject will be traveling to in the near future.

Information regarding a potentially infectious environment is sent to a subject. Alternatively, the information regarding a potentially infectious environment is sent to a third party individual or individuals, for example, a physician or other caregiver. Upon receiving and/or sensing data regarding a potentially infectious environment, the controller may analyze the incoming data and determine that administration of the pharmaceutical composition is appropriate under the current or predicted conditions. The controller may direct the aerosol generator to automatically administer the pharmaceutical composition. In a further aspect, the controller may inform a subject and/or third party caregiver of the current or predicted conditions and the subject and/or third party caregiver may choose to administer the pharmaceutical composition.

The pharmaceutical composition is administered as two or more distinct and non-overlapping particle size ranges configured to contact two or more levels of the pulmonary tissue and as such achieve two or more selected pH ranges in the two or more levels of the pulmonary tissue. In this manner, different pHs may be achieved in different portions of the lung and may facilitate directed treatment of that portion of the lung that is infected by the virus while maintaining the microenvironment in other parts of the respiratory system. For example, avian H5N1 influenza virus preferentially infects cells expressing the 2-3-linked siayly-galactosyl moieties and infects a different portion of the human lung relative to human influenza virus. Based on analysis of autopsied human lung tissue, avian H5N1 influenza preferentially infects human Type II pneumocytes found deep in the lower respiratory tract (see, e.g., Uiprasertkul, et al., Emerging Infectious Dis. 11:1036-1041, 2005, which is incorporated herein by reference). The first particle type of the composition may include one or more liposomes loaded with a buffer that achieves a pH of greater than 7.0, and is sized by milling, formulation or aerosolization for deposition into the alveolar spaces with a diameter of about 1 μm. In contrast, the second particle type of the composition may include liposomes loaded with a buffer or acid or base or combination thereof the achieves a pH ranging from 6.5 to 7.5, and is sized by milling, formulation, or aerosolization to a larger diameter of about 5 μm, for deposition in the upper and conducting airways to maintain a normal pH level.

Example 5

A pulmonary condition in a subject, such as a viral infection, may be prevented and/or treated by administering a pharmaceutical composition that includes one or more membrane selective for a charged ion configured to achieve a selected pH of a pulmonary tissue a subject and that further includes one or more viral homing entities. The one or more membrane selective for a charge ion may be one or more liposomes generated as described herein and loaded with one or more buffering agent to achieve a selected pH. The one or more viral homing entities direct the one or more liposomes of the pharmaceutical composition to a specific location. The specific location may be a viral particle and or a targeted host cell of the subject. The one or more viral homing entities associated with the liposomes may bind to a surface molecule of the virus. Alternatively, the one or more viral homing entities associated with the liposomes may bind to a cell or tissue of a subject that is either already infected with a virus or is susceptible to viral infection. The liposomes of the pharmaceutical composition are administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

The liposomes of the pharmaceutical composition administered to a subject may be linked to one or more viral homing entities. The viral homing entity may bind to a surface molecule of the virus, for example, a viral protein or proteins associated with the outer surface of the viral particle. Examples of viral surface proteins include but are not limited to influenza A hemagglutinin and neuraminidase and rhinovirus capsid proteins VP1, VP2, VP3, and VP4. Alternatively, the viral homing entity may bind to a cell or cells in the pulmonary tissue of a subject that is either already virally infected or is susceptible to viral infection such as, for example, pulmonary epithelial cells. For example, the viral homing entity may recognize a protein that is normally expressed on epithelial cells such as, for example, Epithelial Membrane Antigen (MUC-1), Epithelial Specific Antigen (ESA), Epithelium-specific Cell Surface Glycoprotein, Epithelial Sodium Channels, Surfactant Protein, to name a few. Alternatively, the viral homing entity may recognize a protein on the surface of the target cell that is upregulated, for example, in response to the viral infection. For example, rhinovirus induces increased expression of intercellular adhesion molecule ICAM-1 primary bronchial epithelial cells.

The viral homing entity may be at least a portion of an antibody or fragments thereof, antibody-coated liposome, polynucleotide, polypeptide, receptor, viral plasmid, polymer, protein, toxin, lectin, or any combination thereof that specifically binds to either one or more viral surface protein or one or more target cells or a combination thereof. For example, the viral homing entity may be a commercially available antibody to hemagglutinin (from, e.g., Santa Cruz Biotechnology, Inc., Santa Cruz, Calif.; Prosci, Inc., Poway, Calif.; United States Biological, Swampscott, Mass.). In another aspect, the viral homing entity may be a biomolecue that naturally interacts with one or more components of a viral particle or the target cells. The viral homing entity may consist of one or more α-sialosides that specifically interact with influenza hemagglutinin. Alternatively, the viral homing entity may be a peptide. Novel peptides that bind selective targets may be generated using phage display methodologies (see, e.g., Spear, et al., *Cancer Gene Ther.* 8:506-511, 2001, which is incorporated herein by reference). In some aspects, the viral homing entity may be a synthetic, small molecule compound that binds to a viral protein. Examples of small molecule inhibitors include, but are not limited to, antiviral agents oseltamivir, zanamivir and peramivir that interact with influenza neuroaminidase.

The pharmaceutical composition may include one or more liposomes modified with one or more viral homing entities wherein the viral homing entities are one or more antibodies. Antibodies may be added to liposomes using cross-linking agents and protein A, (see, e.g., Renneisen, et al., *J. Bio. Chem.,* 265:16337-16342, 1990, which is incorporated herein by reference). The liposomes are formed from dry lipid in the presence of an aqueous solution, e.g., a buffer of appropriate pH followed by extrusion through a high pressure device fitted with a polycarbonate filter with the desired pore size to form liposomes of a specific size range. The liposomes are modified with N-succinimidyl 3-(2-pyridyldithio)propionate-modified protein A. The liposomes modified as such are treated with one or more antibodies directed against a viral or host cell target. The one or more antibodies are linked to the liposomes through selective binding to the protein A.

The pharmaceutical composition containing liposomes is administered as two or more distinct and non-overlapping particle size ranges configured to contact two or more levels of the pulmonary tissue and achieve two or more selected pH ranges in the two or more levels of the pulmonary tissue. One or more of the distinct particle sizes of the pharmaceutical composition may be modified with the viral homing entity. The particle sizes and pH ranges selected are dependent upon the type of virus that has been encountered or is expected to be encountered and the relative location of the infection of that virus within the respiratory tract as provided herein. The particle size configured to target that part of the respiratory tract likely to be involved in viral infection may be selectively modified with the one or more viral homing entities to enhance targeting of that portion of the pharmaceutical composition to the infection site.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The herein described components (e.g., steps), devices, and objects and the description accompanying them are used as examples for the sake of conceptual clarity and that various configuration modifications using the disclosure provided herein are within the skill of those in the art. Consequently, as used herein, the specific exemplars set forth and the accompanying description are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable", to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for modulating pH of a virus-infected pulmonary tissue in a mammalian or avian subject to treat a pulmonary viral infectious disease comprising:

generating an aerosol dose of the pharmaceutical composition from an aerosol generator to contact the virus-infected pulmonary tissue in the subject with a pharmaceutical composition including at least one agent, wherein the pharmaceutical composition includes a membrane selective for the charged ion and is configured to achieve a selected pH of the pulmonary tissue, wherein the membrane selective for the charged ion includes liposome membranes of two or more distinct and non-overlapping particle size ranges configured to contact two or more levels of the pulmonary tissue, wherein a first particle size of the two or more distinct and non-overlapping particle size ranges contacts an upper airway passage of the pulmonary tissue in the subject and a second particle size of the two or more distinct and non-overlapping particle size ranges contacts a lower airway passage of the pulmonary tissue in the subject, and operably coupling the aerosol generator to at least one of a heating, ventilation, or air conditioning system to allow delivery of the aerosol dose of the pharmaceutical composition through the system.

2. The method of claim 1, wherein the selected pH of the pulmonary tissue is basic.

3. The method of claim 1, wherein the selected pH of the pulmonary tissue ranges from about 6.5 to 7.5.

4. The method of claim 1, wherein the membrane is configured to alter selectivity for the charged ion in response to a sensed condition in the pulmonary tissue.

5. The method of claim 1, wherein the pharmaceutical composition including the membrane is transmitted based upon an existing pH of the pulmonary tissue.

6. The method of claim 1, wherein the charged ion is released based upon an existing pH of the pulmonary tissue.

7. The method of claim 1, wherein membrane integrity is broken based upon an existing pH of the pulmonary tissue.

8. The method of claim 4, wherein a sensor is configured to monitor the sensed condition in the pulmonary tissue of the subject.

9. The method of claim 8, wherein the sensor is configured to monitor at least one of pH of the pulmonary tissue or pH of an exhalant.

10. The method of claim 8, wherein the sensor is configured to monitor at least one of humidity of an exhalant, temperature, breathing rate, peak rate of exhalation, tidal volume, vital capacity, inspiratory capacity, expiratory reserve volume, or residual volume.

11. The method of claim 8, wherein a controller responsive to the sensor is configured to selectively control delivery of the charged ion to the pulmonary tissue.

12. The method of claim 11, wherein the controller is configured to selectively control delivery of the membrane particle size range.

13. The method of claim 11, wherein the controller is configured to selectively control delivery of one or more membrane particle size ranges.

14. The method of claim 11, wherein the controller is configured to deliver one or more membrane particles of the selected pH.

15. The method of claim 9, wherein the pH-monitoring sensor is in an airway passage of the subject.

16. The method of claim 9, wherein the pH-monitoring sensor is in a sinus or a nostril of the subject.

17. The method of claim 8, further comprising sensing an environmental condition wherein the pharmaceutical composition is administered in response to the sensed environmental condition.

18. The method of claim 17, wherein the sensed environmental condition includes a potentially infectious environment.

19. The method of claim 1, wherein the pulmonary tissue includes an epithelial tissue, mesenchymal tissue, or endothelial tissue.

20. The method of claim 1, further comprising administering the pharmaceutical composition to oropharynx tissue or nasopharynx tissue.

21. The method of claim 1, further comprising administering the pharmaceutical composition to trachial tissue.

22. The method of claim 1, wherein the pulmonary tissue includes bronchial, bronchiole, alveolar duct, or alveoli tissue.

23. The method of claim 1, wherein the charged ion includes a cation.

24. The method of claim 23, wherein the cation includes $H^+$, $K^+$, or $Mg^{2+}$.

25. The method of claim 1, wherein the charged ion includes an anion.

26. The method of claim 25, wherein the anion includes phosphate, citrate, lactate, pyruvate, or an organic acid.

27. The method of claim 1, wherein the pharmaceutical composition includes a buffering agent.

28. The method of claim 27, wherein the buffering agent includes at least one of a phosphate buffer, citrate buffer, lactate buffer, pyruvate buffer, or an organic acid buffer.

29. The method of claim 9, wherein the liposome membrane is configured to communicate to the pH-monitoring sensor.

30. The method of claim 29, wherein the liposome membrane releases a basic agent, an acidic agent or a buffering agent or combination thereof indicating a pH range, and the pH-monitoring sensor is configured to recognize the marker.

31. The method of claim 1, wherein the pharmaceutical composition is administered orally or nasally.

32. The method of claim 1, wherein the pharmaceutical composition is administered as a continuous or pulsatile dose of the pharmaceutical composition.

33. The method of claim 1, comprising delivering the aerosol dose of the pharmaceutical composition to one or more subjects in an enclosed space.

34. The method of claim 1, wherein the pharmaceutical composition is configured to provide a timed-release of the charged ion.

35. The method of claim 1, wherein the pharmaceutical composition is configured to provide an extended release form of the charged ion.

36. The method of claim 1, wherein the pharmaceutical composition is a liquid or a powder.

* * * * *